(12) United States Patent
Nelson et al.

(10) Patent No.: US 7,993,839 B2
(45) Date of Patent: Aug. 9, 2011

(54) METHODS AND KITS FOR REDUCING NON-SPECIFIC NUCLEIC ACID AMPLIFICATION

(75) Inventors: John Richard Nelson, Clifton Park, NY (US); Robert Scott Duthie, Schenectady, NY (US); Sonali Jagdish Shah, Avon, CT (US); Clifford Leslie Smith, Hertfordshire (GB)

(73) Assignee: General Electric Company, Niskayuna, NY (US)

( * ) Notice: Subject to any disclaimer, the term of this patent is extended or adjusted under 35 U.S.C. 154(b) by 16 days.

(21) Appl. No.: 12/337,746

(22) Filed: Dec. 18, 2008

(65) Prior Publication Data

US 2009/0130720 A1 May 21, 2009

Related U.S. Application Data

(63) Continuation-in-part of application No. 11/957,534, filed on Dec. 17, 2007, and a continuation-in-part of application No. 10/466,580, filed on Jul. 15, 2003, now abandoned.

(30) Foreign Application Priority Data

Jan. 19, 2001 (GB) .................................. 200101397
Jan. 15, 2008 (WO) ...................... PCT/GB02/00144

(51) Int. Cl.
*C12Q 1/68* (2006.01)
*C12P 19/34* (2006.01)

(52) U.S. Cl. .......................................... 435/6; 435/91.2

(58) Field of Classification Search ........................ None
See application file for complete search history.

(56) References Cited

U.S. PATENT DOCUMENTS

2004/0209299 A1* 10/2004 Pinter et al. ...................... 435/6
2006/0073511 A1* 4/2006 Jones et al. ....................... 435/6
2006/0216724 A1* 9/2006 Christians et al. ............... 435/6

* cited by examiner

*Primary Examiner* — Kenneth R. Horlick
*Assistant Examiner* — David Thomas
(74) *Attorney, Agent, or Firm* — Jenifer E. Haeckl

(57) ABSTRACT

Methods and kits for efficient amplification of nucleic acids are provided. The methods comprise in-vitro amplification of a nucleic acid template employing partially constrained primers having terminal mismatch primer-dimer structure. The methods also comprise in-vitro amplification of a nucleic acid template employing partially constrained primers having nucleotide analogues. The methods enhance efficiency of nucleic acid amplification reaction by reducing non-specific amplification reactions.

28 Claims, 9 Drawing Sheets

| PRIMER SEQUENCE | HYBRIDIZATION PATTERN | PRIMER-DIMER STRUCTURES | | | | TERMINAL MISMATCH |
|---|---|---|---|---|---|---|
| 5'           3'<br>W N N N S<br>(Pentamer Primer) | 1 | W<br>S | N<br>N | N<br>N | S<br>W | Yes |
| | 2 | W | N<br>S | N<br>N | S<br>N | W | No |
| 5'           3'<br>W W N N S<br>(Hexamer Primer) | 1 | W<br>S | W<br>N | N<br>N | N<br>N | S<br>W | Yes |
| | 2 | W | W<br>S | N<br>N | N<br>N | S<br>W | W | Yes |
| | 3 | W | W | N<br>S | N<br>N | N<br>N | S<br>N | W W | No |
| 5'           3'<br>W W W N N N S<br>(Heptamer Primer) | 1 | W<br>S | W<br>N | W<br>N | N<br>N | N<br>N | N<br>W | S<br>W | Yes |
| | 2 | W | W<br>S | W<br>N | N<br>N | N<br>N | N<br>N | S<br>W | W | Yes |
| | 3 | W | W | W<br>S | N<br>N | N<br>N | N<br>N | N<br>N | S<br>W | W W | Yes |
| | 4 | W | W | W | N<br>S | N<br>N | N<br>N | N<br>N | N<br>N | S<br>N | W W W | No |

1 - Hybridization with no recessed ends
2 - Hybridization with single nucleotide base 3' recessed ends
3 - Hybridization with two nucleotide base 3' recessed ends
4 - Hybridization with three nucleotide base 3' recessed ends

METHODS AND KITS FOR REDUCING NON-SPECIFIC NUCLEIC ACID AMPLIFICATION

CROSS REFERENCE TO RELATED APPLICATIONS

This application is a continuation-in-part of U.S. patent application Ser. No. 10/466,580, filed on Jul. 15, 2003, which claims priority to international Patent Application No. PCT/GB02/00144, filed on Jan. 15, 2002, which claims priority to GB Patent Application No. GB200101397, filed on Jan. 19, 2001, entitled "Suppression of non-specific nucleic acid amplification", and U.S. patent application Ser. No. 11/957,534, filed on Dec. 17, 2007, entitled "Contamination-free reagents for nucleic acid amplification".

FIELD OF INVENTION

The invention generally relates to methods and kits for reducing non-specific nucleic acid amplification for use in the field of nucleic acid amplification and detection. The methods described herein help to reduce primer interactions (e.g., primer-dimer structure formation) during nucleic acid amplification reactions, and thus reduce formation of false amplification products and background signals.

BACKGROUND

A variety of techniques are currently available for efficient amplification of nucleic acids even from a few molecules of a starting nucleic acid template. These include polymerase chain reaction (PCR), ligase chain reaction (LCR), self-sustained sequence replication (3SR), nucleic acid sequence based amplification (NASBA), strand displacement amplification (SDA), multiple displacement amplification (MDA), or rolling circle amplification (RCA). Many of these techniques involve an exponential amplification of the starting nucleic acid template, and generate a large number of amplified products in a short span of time.

Nucleic acid amplification techniques are often employed in nucleic acid-based assays used for analyte detection, sensing, forensic and diagnostic applications, genome sequencing, whole-genome amplification, and the like. Such applications often require amplification techniques having high specificity, sensitivity, accuracy, and robustness. However, most of the currently available techniques for nucleic acid amplification suffer from high background signals, which are generated by non-specific amplification reactions yielding undesired/false amplification products. These non-specific amplification reactions hinder effective utilization of many of these techniques in critical nucleic acid-based assays. For example, if such an amplification reaction were used for diagnostic applications, a false-positive amplification (e.g., formation of amplification products even when the template nucleic acid is absent) may likely result in a wrong diagnosis. Such non-specific, background amplification reactions become even more problematic where the target nucleic acid to be amplified is available only in limited quantities (e.g., whole-genome amplification from a single DNA molecule).

Non-specific, background amplification reactions may be due to exogenous, non-target amplification (e.g., amplification of a contaminating nucleic acid), amplification of untargeted sequences, or primer amplification (endogenous factors). A frequent source of non-specific amplification in a nucleic acid amplification reaction results from various primer gymnastics. A primer may hybridize to regions of a nucleic acid (either in a target nucleic acid itself or in a contaminating nucleic acid) that share some homology with a targeted sequence of the target nucleic acid. If the 3' end of a primer has sufficient homology to an untargeted region, the untargeted region may get amplified. Non-specific amplification may also result from nucleic acid template-independent primer-primer interactions. Primers may form primer-dimer structures by intra- or inter-strand primer annealing (intra molecular or inter molecular hybridizations), and may get amplified. The resultant spurious primer extension products may further get amplified, and may sometimes predominate, inhibit, or mask the amplification of the targeted sequence. In addition, during amplification reaction, the amplification products may self-hybridize, allowing the nucleic acid polymerase to generate hybrid products or chimeric products.

Random primers (e.g., $N_6$, where N=A/T/G/C) are often used for nucleic acid amplification that demands amplification without significant sequence bias. They are useful for applications such as whole-genome amplification, or for amplification of a target nucleic acid with unknown sequence. However, such random primers are also most susceptible for primer-dimer structure formation, and thus lead to higher levels of non-specific, endogenous background amplification. Hence, the use of random primers in high efficiency nucleic acid amplification techniques is often problematic. Constrained-randomized primers that cannot cross-hybridize via intra- or inter-molecular hybridization (e.g., $R_6$, where R=A/G) have been used for suppressing primer-dimer structure formation during nucleic acid amplification. However, such constrained-randomized primers impart considerable bias in nucleic acid amplification reaction in terms of sequence coverage. Such primers are also of limited use for sequence-non-specific or sequence-non-biased nucleic acid amplification reactions (e.g., amplification of whole-genome, or amplification of a nucleic acid with unknown sequence). Thus, there exists a need for developing efficient nucleic acid amplification methods that have lower bias in terms of sequence coverage, and have lower levels of non-specific, background amplification. Development of primers that reduce primer-primer interaction, and can support nucleic acid amplification without sequence bias is also needed.

BRIEF DESCRIPTION

One or more of the embodiments of the invention provide methods and kits for efficient amplification of nucleic acids. In some embodiments, methods for nucleic acid amplification employing primers having terminal mismatch primer-dimer structure are provided. In some embodiments, the method comprises the steps of providing a nucleic acid template, contacting the nucleic acid template with a partially constrained primer having a terminal mismatch primer-dimer structure, and amplifying the nucleic acid template.

In some embodiments, methods for isothermal nucleic acid amplifications using a partially constrained primer comprising a nucleotide analogue are provided. In some embodiments, the method comprises the steps of providing a nucleic acid template, contacting the nucleic acid template with a partially constrained primer comprising a nucleotide analogue, and amplifying the nucleic acid template under isothermal conditions.

In some embodiments, methods for nucleic acid amplification are provided, comprising the steps of providing a nucleic acid template; contacting the nucleic acid template with a nuclease-resistant, partially constrained primer to form a nucleic acid template-primer complex; contacting the nucleic acid template-primer complex with a Phi29 polymerase and deoxyribonucleoside triphosphates; and amplifying the nucleic acid template. In some embodiments, the nuclease-resistant, partially constrained primer comprises a modified nucleotide, and also provides a terminal mismatch primer-dimer structure.

In some embodiments, kits for nucleic acid amplification are provided. In some embodiments, the kit comprises a nucleic acid polymerase and a partially constrained primer having a terminal mismatch primer-dimer structure.

DRAWINGS

These and other features, aspects, and advantages of the present invention will become better understood when the following detailed description is read with reference to the accompanying drawings in which like characters represent like parts throughout the drawings, wherein:

FIG. 1 is a schematic illustration of some of the possible primer-dimer structures that a partially constrained primer having terminal mismatch primer-dimer structure may generate according to one embodiment of the invention.

DETAILED DESCRIPTION

Figure 2:
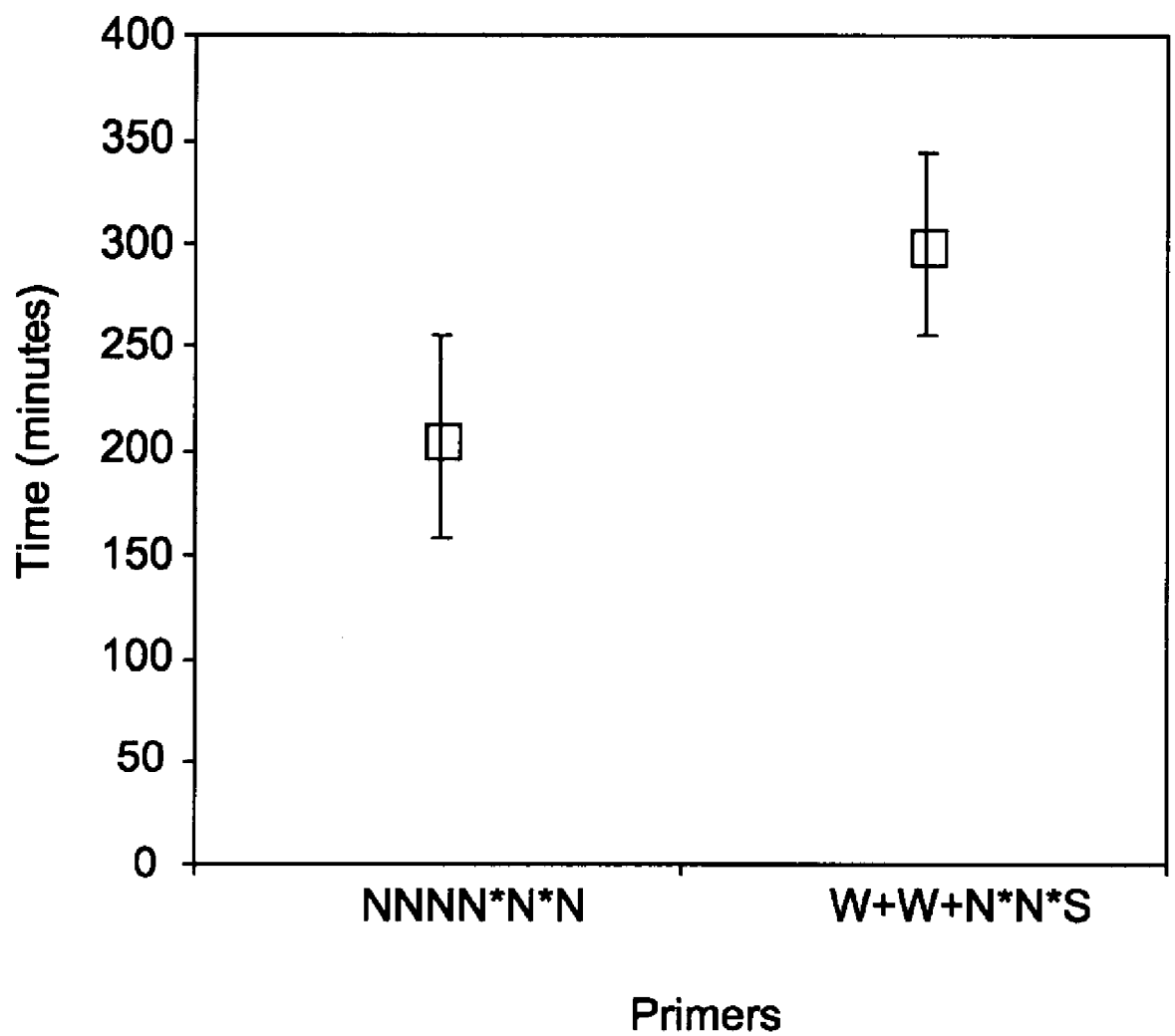
FIG. 2 shows a no template control (NTC) deoxyribonucleic acid (DNA) amplification reaction illustrating the reduction of non-specific nucleic acid amplification according to one embodiment of the invention. The figure illustrates the use of a partially constrained primer comprising LNA nucleotides that has a terminal mismatch primer-dimer structure.

Nucleic acid-based assays involving single molecule DNA amplification or whole-genome amplification demand highly efficient nucleic acid amplification methods that have high yield, high fidelity and have little bias in terms of sequence coverage. A variety of methods that are currently available for use include, but are not limited to, polymerase chain reaction (PCR), ligase chain reaction (LCR), self-sustained sequence replication (3SR), nucleic acid sequence based amplification (NASBA), strand displacement amplification (SDA), and rolling circle amplification (RCA). Isothermal nucleic acid amplification reactions such as rolling circle amplification (RCA), or multiple displacement amplification (MDA) employing random primers are more adaptable than temperature-dependent nucleic acid amplification reaction (e.g., PCR) for such applications. However, these methods often yield a dominant background signal due to undesired non-specific nucleic acid amplification reactions, especially when the concentration of target nucleic acid template is lower (e.g., below 1 ng).

One or more embodiments of the present invention are directed at methods and kits for efficient amplification of nucleic acids. In some embodiments, the methods describe in-vitro amplification of a nucleic acid template that employ partially constrained primers having terminal mismatch primer-dimer structure. In some embodiments, the methods disclose in-vitro amplification of a nucleic acid template employing partially constrained primers having nucleotide analogues. The methods enhance the efficiency and sensitivity of a nucleic acid amplification reaction by reducing non-specific amplification kinetics.

To more clearly and concisely describe and point out the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural references unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts while still being considered free of the modified term. Where necessary, ranges have been supplied, and those ranges are inclusive of all sub-ranges there between.

As used herein, the term "nucleoside" refers to a glycosylamine compound wherein a nucleic acid base (nucleobase) is linked to a sugar moiety. The nucleic acid base may be a natural nucleobase or a modified/synthetic nucleobase. The nucleic acid base includes, but not limited to, a purine base (e.g., adenine or guanine), a pyrimidine (e.g., cytosine, uracil, or thymine), or a deazapurine base. The nucleic acid base may be linked to the 1' position, or at an equivalent position of a pentose (e.g., a ribose or a deoxyribose) sugar moiety. The sugar moiety includes, but is not limited to, a natural sugar, a sugar substitute (e.g., a carbocyclic or an acyclic moiety), a substituted sugar, or a modified sugar (e.g., bicyclic furanose unit as in LNA nucleotide). The nucleoside may contain a 2'-hydroxyl, 2'-deoxy, or 2',3'-dideoxy forms of the sugar moiety.

As used herein the terms "nucleotide" or "nucleotide base" refer to a nucleoside phosphate. It includes, but is not limited to, a natural nucleotide, a synthetic nucleotide, a modified nucleotide, or a surrogate replacement moiety (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP) or a ribonucleoside triphosphate (NTP). The nucleotides may be represented using alphabetical letters (letter designation), as described in Table 1. For example, A denotes adenosine (i.e., a nucleotide containing the nucleobase, adenine), C denotes cytosine, G denotes guanosine, and T denotes thymidine. W denotes either A or T/U, and S denotes either G or C. N represents a random nucleotide (i.e., N may be any of A, C, G, or T/U). A plus (+) sign preceding a letter designation denotes that the nucleotide designated by the letter is a LNA nucleotide. For example, +A represents an adenosine LNA nucleotide, and +N represents a locked random nucleotide (a random LNA nucleotide). A star (*) sign preceding a letter designation denotes that the nucleotide designated by the letter is a phosphorothioate modified nucleotide. For example, *N represents a phosphorothioate modified random nucleotide.

TABLE 1

Letter designations of various nucleotides.

| Symbol Letter | Nucleotide represented by the symbol Letter |
| --- | --- |
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "nucleotide analogue" refers to compounds that are structurally similar (analogues) to naturally occurring nucleotides. The nucleotide analogue may have an altered phosphoate backbone, sugar moiety, nucleobase, or combinations thereof. Generally, nucleotide analogues with altered nucleobases confer, among other things, different base pairing and base stacking proprieties. Nucleotide analogues having altered phosphate-sugar backbone (PNA, LNA) often modify, among other things, the chain properties such as secondary structure formation.

As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998.)). The 2' and 4' position of the furanose unit in the LNA nucleotide may be linked by an O-methylene (e.g., oxy-LNA: 2'-O, 4'-C-methylene-β-D-ribofuranosyl nucleotide), a S-methylene (thio-LNA), or a NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations.

As used herein, the term "oligonucleotide" refers to oligomers of nucleotides or derivatives thereof. The term "nucleic acid" as used herein refers to polymers of nucleotides or derivatives thereof. The term "sequence" as used herein refers to a nucleotide sequence of an oligonucleotide or a nucleic acid. Throughout the specification, whenever an oligonucleotide/nucleic acid is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides/nucleic acids may be a DNA, a RNA, or their analogues (e.g., phosphorothioate analogue). The oligonucleotides or nucleic acids may also include modified bases, and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide. The nucleotide adjacent to the terminal nucleotide refers to a nucleotide that is located at a penultimate position from the terminal position.

As used herein, the term "primer", or "primer sequence" refers to a short linear oligonucleotide that hybridizes to a target nucleic acid sequence (e.g., a DNA template to be amplified) to prime a nucleic acid synthesis reaction. The primer may be a RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" or "complete random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown.

As described herein, "partially constrained primer" refers to a mixture of primer sequences, generated by completely randomizing some of the nucleotides of an oligonucleotide sequence (i.e., the nucleotide may be any of A, T/U, C, G, or their analogues) while restricting the complete randomization of some other nucleotides (i.e., the randomization of nucleotides at certain locations are to a lesser extent than the possible combinations A, T/U, C, G, or their analogues). For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As described herein, the term "partially constrained primer having a terminal mismatch primer-dimer structure" refers to a partially constrained primer sequence, wherein when two individual primer sequences in the partially constrained primer hybridize each other inter-molecularly, with an internal homology of three or more nucleotides, to form a primer-dimer structure having no recessed ends, or a primer-dimer structure having a single-nucleotide base 3' recessed ends, or a primer-dimer structure having a two-nucleotide base 3' recessed ends, there exists a nucleotide mismatch (i.e., nucleotides do not base-pair) at both the 3' terminal nucleotides in the primer-dimer structure. For example, a partially constrained pentamer primer represented by WNNNS provides a terminal mismatch at both the 3' terminal nucleotides when it is inter-molecularly hybridized to form a primer-dimer structure having no recessed ends. In the primer-dimer structure, there exist an internal homology of three nucleotides (i.e., the three random nucleotides in WNNNS may base-pair with each other when the primer-dimer structure having no recessed ends is formed by inter-molecular hybridization). However, this primer example does not provide a terminal mismatch when it is inter-molecularly hybridized to form a primer-dimer structure with single-nucleotide base 3' recessed ends (see FIG. 1; rectangular boxes in the figure illustrates internal homology of the primer-dimer structure). Similarly, a partially constrained hexamer primer represented by WWNNNS provides a terminal mismatch at both the 3' terminal nucleotides when it is inter-molecularly hybridized to form a primer-dimer structure having no recessed ends. Moreover, this primer example provides a terminal mismatch at both the 3' terminal nucleotides even when it is inter-molecularly hybridized to form a primer-dimer structure having a single-nucleotide base 3' recessed ends. A partially constrained heptamer primer represented by WWWNNNS provides a terminal mismatch at both the 3' terminal nucleotides when it is inter-molecularly hybridized to form a primer-dimer structure having no recessed ends. Further, this primer example provides a terminal mismatch at both the 3' terminal nucleotides when it is inter-molecularly hybridized to form a primer-dimer structure having a single-nucleotide base 3' recessed ends, or to form a primer-dimer structure having a two-nucleotide base 3' recessed ends.

As used herein, the term "plasmid" refers to an extra-chromosomal nucleic acid that is separate from a chromosomal nucleic acid. A plasmid DNA may be capable of replicating independently of the chromosomal nucleic acid (chromosomal DNA) in a cell. Plasmid DNA is often circular and double-stranded.

As used herein, the terms "amplification", "nucleic acid amplification", or "amplifying" refer to the production of multiple copies of a nucleic acid template, or the production of multiple nucleic acid sequence copies that are complementary to the nucleic acid template.

As used herein, the term "target nucleic acid" refers to a nucleic acid that is desired to be amplified in a nucleic acid amplification reaction. For example, the target nucleic acid comprises a nucleic acid template.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction, the DNA polymerase needs a primer to which it can add the first nucleotide. Suitable primers comprise oligonucleotides of RNA or DNA. The DNA polymerases may be a naturally occurring DNA polymerases or a variant of natural enzyme having the above-mentioned activity. For example, it may include a DNA polymerase having a strand displacement activity, a DNA polymerase lacking 5'→3' exonuclease activity, a DNA polymerase having a reverse transcriptase activity, or a DNA polymerase having an endonuclease activity.

As used herein the term "proofreading DNA polymerase" refers to any DNA polymerase that is capable of correcting its errors while performing DNA synthesis. A proofreading DNA polymerase possesses a 3→5' exonuclease activity apart from its polymerase activity, and this exonuclease activity is referred as proofreading activity. Proofreading activity of such polymerases correct mistakes in the newly synthesized DNA. During DNA synthesis, when an incorrect base pair is recognized, the proofreading DNA polymerase reverses its direction by one base pair of DNA. The 3→5' exonuclease activity (proofreading activity) of the enzyme allows the incorrect nucleotide base pair to be excised. Following the nucleotide base excision, the polymerase re-inserts the correct nucleotide base, and continues the DNA synthesis. When free dNTPs are present in the solution or reaction mixture suitable for DNA synthesis, the primary activity of the proofreading DNA polymerase is DNA synthesis. However, when dNTPs are not available for the DNA synthesis reaction, the primary activity of the proofreading DNA polymerase may be its 3→5' exonuclease activity. Some of the proofreading DNA polymerases may require the presence of a divalent cation for their proofreading activity as well as for their polymerase activity. Suitable divalent cations that can switch on the proofreading activity of the proofreading polymerases include, but are not limited to, magnesium or manganese.

As used herein, "a strand displacing nucleic acid polymerase" refers to a nucleic acid polymerase that has a strand displacement activity apart from its nucleic acid synthesis activity. That is, a strand displacing nucleic acid polymerase can continue nucleic acid synthesis on the basis of the sequence of a nucleic acid template strand (i.e., reading the template strand) while displacing a complementary strand that had been annealed to the template strand.

As used herein, the term "complementary", when used to describe a first nucleic acid/oligonucleotide sequence in relation to a second nucleic acid/oligonucleotide sequence, refers to the ability of a polynucleotide or oligonucleotide comprising the first nucleic acid/oligonucleotide sequence to hybridize (e.g., to form a duplex structure) under certain hybridization conditions with an oligonucleotide or polynucleotide comprising the second nucleic acid/oligonucleotide sequence. Hybridization occurs by base pairing of nucleotides (complementary nucleotides). Base pairing of the nucleotides may occur via Watson-Crick base pairing, non-Watson-Crick base pairing, or base pairing formed by non-natural/modified nucleotides.

As used herein the term "high stringent hybridization conditions" refer to conditions that impart a higher stringency to an oligonucleotide hybridization event than the stringency provided by conditions that are generally used for nucleic acid amplification reactions. For example, a high stringent hybridization condition may be effected in a nucleic acid amplification reaction by increasing the reaction temperature or by decreasing the salt concentration. Nucleic acid amplification reactions are often carried out at about 75 mM salt concentration. In contrast, if a nucleic acid amplification reaction is performed at about 15 mM salt concentration, it may offer a high stringent hybridization condition. High stringent hybridization condition may be provided in an in-vitro isothermal nucleic acid amplification reaction by increasing the temperature from about 30° C., which is often used. For example, the isothermal nucleic acid amplification reaction may be performed at about 35° C. to about 45° C. to provide a high stringent hybridization condition.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction may be initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatamers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase.

As used herein, multiple displacement amplification (MDA) refers to a nucleic acid amplification method, wherein the amplification involves the steps of annealing a primer to a denatured nucleic acid followed by a strand displacement nucleic acid synthesis. As nucleic acid is synthesized by strand displacement, a gradually increasing number of priming events occur, forming a network of hyper-branched nucleic acid structures. MDA is highly useful for whole-genome amplification for generating high-molecular weight DNA with limited sequence bias from a small amount of genomic DNA sample. Strand displacing nucleic acid polymerases such as Phi29 DNA polymerase or large fragment of the Bst DNA polymerase may be used in multiple displacement amplification. MDA is often performed under isothermal reaction conditions, and random primers are used in the reaction for achieving amplification with limited sequence bias.

As used herein the term "reaction mixture" refers to the combination of reagents or reagent solutions, which are used to carry out a chemical analysis or a biological assay. In some embodiments, the reaction mixture comprises all necessary components to carry out a nucleic acid (DNA) synthesis/amplification reaction.

As used herein, the terms "reagent solution" or "solution suitable for performing a DNA synthesis reaction" refer to any or all solutions, which are typically used to perform an amplification reaction or DNA synthesis. They include, but are not limited to, solutions used in isothermal DNA amplification methods, solutions used in PCR amplification reactions, or the like. The solution suitable for DNA synthesis reaction may comprise buffer, salts, and/or nucleotides. It may further comprise primers and/or a DNA template to be amplified.

One or more embodiments are directed to methods and kits for improved nucleic acid amplification reactions that are less prone to generating false amplification products. These amplification methods are more reliable than currently available amplification techniques and so are more suitable for applications such as amplification of rare sequences (i.e., where target nucleic acids are available in lower amount; e.g., detection of rare mutant sequences within a population of wild-type sequences), or whole genome amplification reactions. The amplification methods use specially designed partially constrained primers to reduce background amplification reactions. Suitable length of the partially constrained primer may be in the range of about 3 nucleotides to about 10 nucleotides long. In some embodiments, the partially constrained primer consists of about 5 nucleotides to about 7 nucleotides.

The partially constrained primers reduce the formation of stable primer-dimer structures under conditions that are commonly used for nucleic acid amplification reactions. The reduction of stable primer-dimer structures that may be extended during nucleic acid amplification reactions, in turn reduces the false amplification reactions. The reduced levels of stable primer-dimer structures in the reaction mixture is achieved by designing the partially constrained primers in such a way that even if the primer-dimer structure is formed in the reaction mixture, it will be formed with a terminal mismatch. In a primer-dimer structure having terminal mismatch, the 3' terminal nucleotides are not base paired, and so is not amenable for primer extension reaction during nucleic acid amplification.

In some embodiments, the partially constrained primer comprises, at suitable locations, nucleic acid analogues that have higher complementary specificity than that of natural nucleotides (e.g., LNA nucleotides). The location of nucleotide analogues in the partially constrained primer is chosen in such a way that it inhibits the formation of stable primer-dimer structures under nucleic acid amplification reaction conditions. Moreover, the nucleotide analogues are positioned such that even if the partially constrained primer hybridizes inter-molecularly (to form a primer-dimer structure), there occurs a terminal mismatch even at high stringent hybridization conditions. Hence, even if primer-dimer structures are formed during nucleic acid amplification reaction, the formed primer-dimer structures with terminal mismatch will not be extended during amplification reaction due to the unpaired 3' terminal nucleotides.

When the partially constrained primer comprising LNA nucleotide is used for nucleic acid amplification reaction, the amplification reaction may be performed at more stringent hybridization conditions. The amplification reaction may be performed at higher temperatures (e.g., above 30° C. for an isothermal nucleic acid amplification), the upper limit being the temperature at which the DNA polymerase used in the reaction may become non-functional. It may also be performed at a lower salt concentration (e.g., about 10 µM to about 25 µM salt concentration) than what is normally used (e.g., about 75 µM salt concentration). Due to higher complementary specificity, the hybridization of the partially constrained primer comprising LNA nucleotides to the target nucleic acid will not be substantially affected by high stringent hybridization conditions. Hence, the amplification of the desired target nucleic acid amplification will also not substantially affected. The amenability of using stringent hybridization conditions further reduces the probability of formation of stable primer-dimer structures, and thus reduces non-specific nucleic acid amplifications.

In some embodiments, improved methods and kits for isothermal nucleic acid amplification are provided. The methods and kits reduce non-specific nucleic acid amplification reactions by reducing primer gymnastics. Non-limiting examples of suitable isothermal nucleic acid amplification reactions comprise rolling circle amplification (RCA) or multiple displacement amplification (MDA). The methods may be used in the amplification of circular nucleic acid templates or linear nucleic acid templates. The methods may be effectively used even when the amount of the nucleic acid template to be amplified is minimal. The methods may be useful in whole-genome amplification or in single nucleic acid amplification reactions.

In one embodiment, a method for nucleic acid amplification is provided that employs a partially constrained primer, which is designed to have a terminal mismatch primer-dimer structure. The method comprises providing a nucleic acid template, contacting the nucleic acid template with a partially constrained primer having a terminal mismatch primer-dimer structure, and amplifying the nucleic acid template. Suitable length of the partially constrained primer may be in the range of about 3 nucleotides to about 10 nucleotides long. In some embodiments, the partially constrained primer may be a tetramer, pentamer, hexamer or a heptamer. A combination of partially constrained primers having varying primer lengths may also be used.

The method may further include the steps of addition of a nucleic acid polymerase and deoxyribonucleoside triphosphates before the amplification step. The nucleic acid template may be amplified using any of a variety of nucleic acid amplification methods. The amplification of the nucleic acid template may be performed using thermal cycling methods, such as polymerase chain reaction (PCR), or it may be performed, at least in part, under isothermal conditions. In some embodiments, the nucleic acid template is amplified using isothermal nucleic acid amplification methods.

The nucleic acid polymerase that is used for amplification may be a proofreading or a non-proofreading nucleic acid polymerase. In some embodiments, the nucleic acid polymerase used is a strand displacing nucleic acid polymerase. The nucleic acid polymerase may be a termophilic or a mesophilic nucleic acid polymerase. Examples of DNA polymerases that are suitable for use include, but are not limited to, Phi29 DNA polymerase, hi-fidelity fusion DNA polymerase (e.g., *Pyrococcus*-like enzyme with a processivity-enhancing domain, New England Biolabs, MA), Pfu DNA polymerase from *Pyrococcus furiosus* (Strategene, Lajolla, Calif.), Bst DNA polymerase from *Bacillus stearothermophilus* (New England Biolabs, Mass.), Sequenase™ variant of T7 DNA polymerase, exo(-)Vent$_R$™ DNA polymerase (New England Biolabs, MA), Klenow fragment from DNA polymerase I of *E. coli*, T7 DNA polymerase, T4 DNA polymerase, DNA polymerase from *Pyrococcus* species GB-D (New England Biolabs, Mass.), or DNA polymerase from *Thermococcus litoralis* (New England Biolabs, Mass.).

In some embodiments, the methods may employ a highly processive, strand-displacing polymerase to amplify the nucleic acid template under conditions for high fidelity base incorporation. A high fidelity DNA polymerase refers to a DNA polymerase that, under suitable conditions, has an error incorporation rate equal to or lower than those associated with commonly used thermostable PCR polymerases such as Vent DNA polymerase or T7 DNA polymerase (from about $1.5\times 10^{-5}$ to about $5.7\times 10^{-5}$). Additional enzymes may be included in the amplification reaction mixture to minimize mis-incorporation events. For example, protein mediated error correction enzymes, such as, MutS, may be added to improve the polymerase fidelity either during or following the polymerase reaction.

The nucleic acid template may be a linear template, nicked template or a circular template. It may be a natural or synthetic nucleic acid. It may comprise a deoxyribonucleic acid (DNA) or a ribonucleic acid (RNA). In some embodiments, the nucleic acid template may be a DNA template. The DNA template may be a cDNA or a genomic DNA. The circular nucleic acid template may be a synthetic template (e.g., a linear or nicked DNA circularized by enzymatic/chemical reactions), or it may be a plasmid DNA. In some embodiments, the method may amplify a circular DNA template by rolling circle amplification. In some other embodiments, a linear DNA template may be amplified using multiple displacement nucleic acid amplification.

In some embodiments, a Phi29 DNA polymerase or Phi29-like polymerase may be used for amplifying a DNA template. In some embodiments, a combination of a Phi29 DNA polymerase and a Taq DNA polymerase may be used for the circular DNA amplification.

The partially constrained primers may be generated by completely randomizing (i.e., the nucleotide base may be any of A, T/U, C, G or their analogues) some nucleotides of an oligonucleotide sequence, while restricting the complete randomization of some other nucleotides (i.e., the randomization of nucleotide bases at certain locations are to a lesser extent than the four possible combinations A, T/U, C or G). The randomization of the nucleotides is restricted in such a way that if the partially constrained primer dimerizes, it forms a primer-dimer structure that has a terminal mismatch. Thus, when two individual primer sequences in the partially constrained primer hybridize to each other inter-molecularly with an internal homology of three or more nucleotide bases, to form a primer-dimer structure having no recessed ends, or a primer-dimer structure having a single-nucleotide base 3' recessed ends, or a primer-dimer structure having a two-nucleotide base 3' recessed ends, there exists a nucleotide mismatch at both the 3' terminal nucleotide bases in the primer-dimer structure (i.e., the 3' terminal nucleotides in the primer dimer structure are unpaired.). This constrained randomization at certain selected nucleotides reduce the probability of the formation of stable primer-dimer structures in the reaction mixture during nucleic acid amplification. Moreover, even if the primer-dimer structures are formed during the nucleic acid amplification reaction, the terminal mismatch at both the 3' terminal nucleotides in the primer-dimer structures hinders any primer extension reaction by the nucleic acid polymerase from those 3' terminal nucleotides.

In some embodiments, randomization of two nucleotides in the partially constrained primer is restricted. In some embodiments, the randomization of more than two nucleotides (e.g., three, four, or five nucleotides) in the partially constrained primer is restricted. The extent of randomization may be empirically determined based on amplification reaction requirements and conditions.

In some embodiments, the partially constrained primer is designed to restrict the randomization of terminal nucleotides. For example, the partially constrained primer may be designed to consist of a sequence, $W(N)_yS$, wherein y=2, 3, 4 or 5. Here, the 5' terminal nucleotide of the primer sequence is restricted to W (i.e., either A or T), and the 3' terminal nucleotide is restricted to S (i.e., either G or C). Since W cannot base pair with S, there will be a terminal mismatch at both the 3' terminal nucleotides if the primer-dimer structure without any recessed ends is formed by inter-molecular hybridization. However, if the primers are inter-molecularly hybridized with at least one-nucleotide base recessed ends, there will not be any terminal mismatch since S or W may base pair with N (i.e., S may base pair with N, when N is G or C; and W may base pair with N, when N is A or T). Non-limiting examples of primers, that have restricted randomization only at the terminal nucleotides include, $W(N)_yS$, $S(N)_yW$, $D(N)_yG$, $G(N)_yD$, $C(N)_yA$, or $A(N)_yC$. The integer value of y may be in the range 2 to 13. In some embodiments, the value of y may be 2, 3, 4, or 5. In one embodiment, the partially constrained primer consists of a hexamer primer, the sequence of which may be WNNNNS, SNNNNW, DNNNNG, GNNNND, CNNNNA, or ANNNNC. In another embodiment, the partially constrained primer consists of a pentamer primer, the sequence of which may be WNNNS, SNNNW, DNNNG, GNNND, CNNNA, or ANNNC.

In some embodiments, the randomization of both of the terminal nucleotides of the partially constrained primer may be restricted along with a restricted randomization of the nucleotide that is adjacent to the 5' terminal nucleotide. For example, the partially constrained primer may be designed to consist of a sequence $WW(N)_yS$, wherein y=2, 3, 4 or 5. Since W cannot base pair with S, there will be a terminal mismatch at both the 3' terminal nucleotides if the primer-dimer structure is formed (via inter-molecular hybridization) without any recessed ends. For some partially constrained primers, primer-dimer structure may have a terminal mismatch even when primer-dimers are formed with recessed 3' ends. For example, if a random primer of the sequence WWNNNS makes a primer-dimer structure even with a single-nucleotide 3' recessed ends, there will exist a nucleotide mismatch at both the 3' terminal nucleotides. This will considerably reduce the probability of stable primer-dimer structures in nucleic acid amplification reactions. Even if such primer-dimer structures are formed during the amplification reaction, nucleic acid synthesis is not feasible from any of the 3' terminal nucleotides. Hence, the non-specific nucleic acid amplification effected by primer-dimer structure formation may be decreased considerably, which in turn may result in lower background amplification. The primers that have restricted randomization at both terminal nucleotides and also at the nucleotide adjacent to the 5' terminal nucleotide include, but are not limited to, $WW(N)_yS$, $SS(N)_yW$, $DD(N)_yG$, $GG(N)_yD$, $CC(N)_yA$, or $AA(N)_yC$. The integer value of y may be in the range 2 to 12. In some example embodiments, the value of y may be 2, 3, or 4. For example, the partially constrained primer may consists of a hexamer primer, the sequence of which may be WWNNNS, SSNNNW, DDNNNG, GGNNND, CCNNNA, or AANNNC. In some embodiments, the partially constrained primer may consists of a pentamer primer, the sequence of which may be WWNNS, SSNNW, DDNNG, GGNND, CCNNA, or AANNC.

In some embodiments, the partially constrained primer may be a nuclease-resistant primer. For example, the partially constrained primer may be resistant to an exonuclease (e.g., a 3→5' exonuclease). In some embodiments, the partially constrained primer includes modification at the sugar-phosphate backbone that makes the primer resistant to the exonuclease digestion. For example, the partially constrained primer may possess one, two, three, or four phosphorothioate linkages between nucleotides that are located toward the 3' end of the primer sequence. In some embodiments, the partially constrained primer contains one phosphorothioate linkage that makes the primer resistant to degradation by an exonuclease. Non-limiting examples include WWNN*S, SSNN*W, DDNN*G, GGNN*D, CCNN*A, AANN*C, WWNNN*S, SSNNN*W, DDNNN*G, GGNNN*D, CCNNN*A, or AANNN*C. In some embodiments, the partially constrained primer contains more than one phosphorothioate linkages in the sugar-phosphate backbone. Examples include partially constrained primer sequences such as, but are not limited to, WWN*N*S, SSN*N*W, DDN*N*G, GGN*N*D, CCN*N*A, AAN*N*C, WWNN*N*S, SSNN*N*W, DDNN*N*G, GGNN*N*D, CCNN*N*A, or AANN*N*C. The modification of the sugar-phosphate backbone in the sequence may be at a 3'-terminal position, or it may be located at a position other than the 3'-terminal position. When the modification is located at positions other than the 3'-terminal end of a partially constrained primer sequence, the 3'-terminal nucleotide may be removed by the 3→5' exonuclease activity of an exonuclease. In some embodiments, multiple partially constrained primers may be used for nucleic acid amplification. The multiple partially constrained primers may be chosen from partially constrained primers sensitive to exonuclease activity, or partially constrained primers resistant to exonuclease activity. In some embodiments, a mixture of partially constrained primers sensitive to exonuclease activity and resistant to exonuclease activity may be used for amplification reaction.

In some embodiments, the partially constrained primer may comprise a nucleotide analogue at a suitable position. In some embodiments, a nucleotide analogue that has higher complementary specificity than that of a natural nucleotide may be used. Non-limiting examples of suitable nucleic acid analogues that may be incorporated in the partially constrained primer include peptide nucleic acids (PNA), 2'-fluoro N3-P5'-phosphoramidates, 1',5'-anhydrohexitol nucleic acids (HNA), or locked nucleic acid (LNA) nucleotides. The location of nucleotide analogues in the partially constrained primer is chosen in such a way that if the partially constrained primer hybridizes inter-molecularly (to form a primer-dimer structure), there occurs a terminal mismatch even at stringent hybridization conditions (e.g., at a temperature that is about 5° C. to about 10° C. higher than a typical nucleic acid amplification reaction condition). Moreover, the nucleotide analogues are positioned such that the formation of stable primer-dimer structures under nucleic acid amplification reaction conditions are substantially inhibited. Due to higher complementary specificity of the nucleotide analogues, a nucleic acid amplification reaction using partially constrained primers comprising nucleotide analogues may be performed at more stringent conditions (e.g. performing the reaction at higher temperatures or lower salt concentration). The partially constrained primer having nucleotide analogues has higher complementary specificity to the target (i.e., The $_m$ of the target nucleic acid-primer complex may be higher when the partially constrained primer comprises the nucleotide analogue). Since such primer hybridizes to the target nucleic acid even at higher temperatures/lower salt concentration, the desired target nucleic acid amplification is not substantially affected under stringent hybridization conditions. Moreover, the amenability of using stringent hybridization conditions for amplification reactions further reduces the probability of formation of stable primer-dimer structures. Furthermore, even if primer-dimer structures are formed during nucleic acid amplification reaction, they will be formed with a terminal mismatch and so will not be extended by the nucleic acid polymerase.

In some embodiments, the partially constrained primer comprises a LNA nucleotide at a suitable position. Suitable LNA nucleotides include, but are not limited to, an oxy-LNA (2'-O, 4'-C-methylene-β-D-ribofuranosyl nucleotide), a thio-LNA (2'-S, 4'-C-methylene-β-D-ribofuranosyl nucleotide), or an amino-LNA (2'-NH, 4'-C-methylene-β-D-ribofuranosyl nucleotide) nucleotide. LNA nucleotide may be located toward the 5' end of the partially constrained primer sequence. The partially constrained primer incorporating LNA nucleotide may form primer-dimer structures with terminal mismatch. In some embodiments, the partially constrained primer comprises two LNA nucleotides. For example, a partially constrained primer may have a LNA nucleotide at the 5' terminal position, and also at the position adjacent to the 5' terminal position. In some other examples, the 5' terminal nucleotide of the partially constrained primer may be a natural nucleotide whereas the next two nucleotides adjacent to the 5' terminal nucleotide may be LNA nucleotides. Non-limiting examples of partially constrained primers comprising LNA nucleotides and having a primer-dimer structure with a terminal mismatch include, +W+WNNS, +S+SNNW, +D+DNNG, +G+GNND, +C+CNNA, +A+ANNC, +W+WNNNS, +S+WNNNW, +D+DNNNG, +G+GNNND, +C+CNNNA. +A+ANNNC, W+W+NNS, S+S+NNW, D+D+NNG, G+G+NND, C+C+NNA, A+A+NNC, W+W+NNNS, S+W+NNNW, D+D+NNNG, G+G+NNND, C+C+NNNA., or A+A+NNNC.

The partially constrained primer comprising a LNA nucleotide may be an exonuclease-resistant primer that is resistant to 3→5' exonuclease activity. They may possess a single or multiple phosphorothioate linkages between nucleotides at the 3' end of the primer sequence. Non limiting examples, include +W+WNN*S, +S+SNN*W, +D+DNN*G, +G+GNN*D, +C+CNN*A, +A+ANN*C, +W+WNNN*S, +S+WNNN*W, +D+DNNN*G, +G+GNNN*D, +C+CNNN*A. +A+ANNN*C, W+W+NN*S, S+S+NN*W, D+D+NN*G, G+G+NN*D, C+C+NN*A, A+A+NN*C, W+W+NNN*S, S+W+NNN*W, D+D+NNN*G, G+G+NNN*D, C+C+NNN*A., A+A+NNN*C, +W+WN*N*S, +S+SN*N*W, +D+DN*N*G, +G+GN*N*D, +C+CN*N*A, +A+AN*N*C, +W+WNN*N*S, +S+WNN*N*W, +D+DNN*N*G, +G+GNN*N*D, +C+CNN*N*A. +A+ANN*N*C, W+W+N*N*S, S+S+N*N*W, D+D+N*N*G, G+G+N*N*D, C+C+N*N*A, A+A+N*N*C, W+W+NN*N*S, S+W+NN*N*W, D+D+NN*N*G, G+G+NN*N*D, C+C+NN*N*A., or A+A+NN*N*C.

In some embodiments, a method for isothermal nucleic acid amplification is provided using a partially constrained primer that comprises a nucleic acid analogue. The method comprises the steps of providing a nucleic acid template; contacting the nucleic acid template with a partially constrained primer, wherein the partially constrained primer comprises a nucleotide analogue; and amplifying the nucleic acid template under isothermal conditions.

The partially constrained primer may be a partially constrained primer having a terminal mismatch primer-dimer structure. In one embodiment, the partially constrained primer is designed such that the nucleotides at 3' terminal position and 5' terminal position are non-complementary to each other. The 3' terminal nucleotide of the partially constrained primer may further be non-complementary to a nucleotide adjacent to the 5' terminal nucleotide. In some embodiments, the partially constrained primer consisting of a nucleotide sequence $(W)_x(N)_y(S)_z$ may be employed. In this sequence, x, y and z are integer values independent of each other. In some embodiments, the values of x, y, and z in $(W)_x(N)_y(S)_z$ may be x=2 or 3; y=2, 3 or 4; and z=1 or 2 respectively.

In some embodiments, the nucleotide analogue in the partially constrained primer comprises a LNA nucleotide. Non-limiting examples include +W+WNNS, W+W+NNS, +W+WNNNS, or W+W+NNNS. In some embodiments, the partially constrained primer may be an exonuclease-resistant primer. In one embodiment, the partially constrained primer comprises a phosphorothioate linkage between a 3' terminal nucleotide and a nucleotide that is adjacent to the 3' terminal nucleotide. In some other embodiments, multiple phosphorothioate linkages may be present in the sequence. Non-limiting examples include W+W+NN*S, +W+WNN*S, W+W+NNN*S, +W+WNNN*S, W+W+N*N*S, +W+WN*N*S, W+W+NN*N*S, or +W+WNN*N*S.

The nucleic acid template may be a single-stranded nucleic acid template or it may be a double-stranded nucleic acid template. It may be a circular nucleic acid template, a nicked nucleic acid template, or a linear nucleic acid template. The nucleic acid template may comprise a DNA, an RNA or a DNA-RNA chimeric template. The nucleic acid template may be a synthetic nucleic acid or a natural nucleic acid. It may also comprise modified nucleotides. The nucleic acid DNA template may be derived from a genomic DNA, an RNA template (using reverse transcriptase enzymes) or a cDNA. In one example embodiment, the nucleic acid template is a circular DNA template.

Non-limiting examples of isothermal nucleic acid amplification methods include ligase chain reaction (LCR), self-sustained sequence replication (SSR), nucleic acid sequence-based amplification (NASBA), loop-mediated isothermal amplification (LAMP), amplification with Qb-replicase, or the like. In some embodiments, the nucleic acid template is amplified using strand displacement amplification reaction (SDA). In some embodiments, the nucleic acid template is amplified using multiple displacement amplification (MDA). In one embodiment, the nucleic acid template is amplified using rolling circle amplification (RCA) method. Rolling circle amplification that could be used may be a linear RCA (LRCA) or it may be an exponential RCA (ERCA). In another embodiment, multiply primed rolling circle amplification (MPRCA) is employed for amplifying the nucleic acid template.

The nucleic acid polymerase that may be employed in the isothermal nucleic acid amplification reaction may be a prokaryotic, fungal, viral, bacteriophage, plant, or eukaryotic nucleic acid polymerase. Suitable nucleic acid polymerases may also comprise holoenzymes, functional portions of the holoenzymes, chimeric polymerase, or any modified polymerase that can effectuate the synthesis of a nucleic acid molecule. Non-limiting examples of suitable DNA polymerases that may be used include bacteriophage Phi29 DNA polymerase, Phi29-like polymerases (e.g., Phage M2 DNA polymerase, Phage B103 DNA polymerase, or Phage GA-1 DNA polymerase), phage Phi-PRD1 polymerase, Vent DNA$_R$™ polymerase (New England Biolabs, MA), Deep Vent$_R$™ DNA polymerase (New England Biolabs, MA), KlenTaq® DNA polymerase, DNA polymerase I, DNA polymerase I modified with T7 DNA polymerase sequences, Klenow fragment of DNA polymerase I, DNA polymerase III, DNA polymerase III holoenzymes, T5 DNA polymerase, T4 DNA polymerase holoenzymes, T7 DNA polymerase, genetically engineered T7 DNA polymerase having reduced or insignificant 3→5' exonuclease activity (e.g., Sequenase™ DNA polymerase), DNA polymerase form *Thermoanaerobacter thermohydrosulfuricus* (Tts DNA polymerase), or fragment thereof, modified Tts DNA polymerase, Bst polymerase, rBST DNA polymerase, N29 DNA polymerase, or TopoTaq DNA polymerase.

In some embodiments, wherein the DNA template is a circular DNA template, the circular DNA template may be amplified using a rolling circle amplification method. Rolling circle amplification that may be suitable to use with the present invention includes a linear RCA (LRCA) or an exponential RCA (ERCA). In some example embodiments, multiply primed rolling circle amplification (MPRCA) is employed for amplifying the circular DNA template. In some embodiments, a ligation rolling circle amplification is employed for amplifying the circular DNA template. The rolling circle amplification of the circular DNA template may yield a concatamer comprising tandem repeat units of DNA template sequence.

The DNA polymerase that may be used to amplify the circular DNA template may be, but is not limited to, a proofreading DNA polymerase or a non-proofreading DNA polymerase. In some embodiments, the proofreading DNA polymerase comprises a thermally stable DNA polymerase. Proofreading DNA polymerase may be a thermophilic DNA polymerase or a mesophilic DNA polymerase. In some embodiments, a combination of a proofreading DNA polymerase and a non-proofreading DNA polymerase may be used for efficient amplification of the DNA template. Any suitable proofreading DNA polymerase may be used. Examples of proofreading polymerases that are suitable for use include, but are not limited to, Phi29 DNA polymerase, hi-fidelity fusion DNA polymerase (e.g., *Pyrococcus*-like enzyme with a processivity-enhancing domain from New England Biolabs, MA), Pfu DNA polymerase from *Pyrococcus furiosus* (Strategene, Lajolla, Calif.), Klenow fragment from DNA polymerase I of *E. coli*, T7 DNA polymerase, T4 DNA polymerase, DNA polymerase from *Pyrococcus* species GB-D (New England Biolabs, MA) and DNA polymerase from *Thermococcus litoralis* (New England Biolabs, MA). Suitable examples of non-proofreading DNA polymerase that could be used include, but are not limited to Taq DNA polymerase, Tts DNA polymerase, large fragment of Bst DNA polymerase, exo (−) DNA Polymerase gene from *Pyrococcus* species GB-D (New England Biolabs, MA), or exo (−) DNA Polymerase from *Thermococcus litoralis* (New England Biolabs, MA).

In some embodiments, a nucleic acid amplification is provided, wherein the method comprises the steps of providing a nucleic acid template; contacting the nucleic acid template with a nuclease-resistant, partially constrained primer to form a nucleic acid template-primer complex; contacting the nucleic acid template-primer complex with a Phi29 polymerase and deoxyribonucleoside triphosphates; and amplifying the nucleic acid template. The nuclease-resistant, partially constrained primer comprises a modified nucleotide and has a terminal mismatch primer-dimer structure. The nucleic acid template may be amplified by rolling circle nucleic acid amplification, or by multiple displacement nucleic acid amplification.

In some embodiments, the nucleic acid template is amplified to generate an amplified nucleic acid, in a solution suitable for performing a nucleic acid amplification reaction. The amplification reaction often employs reagents such as a primer, a nucleic acid polymerase, and free nucleotides (e.g., dNTPs). The nucleic acid polymerase that is employed in the amplification reaction may be a proofreading nucleic acid polymerase. In some embodiments, each of the reagents used in the nucleic acid amplification reaction may be pre-treated to remove any contaminating nucleic acid sequences. In some embodiments, pre-treatment of the reagents includes incubating the reagents in presence of Ultra-Violet radiation. In some embodiments, the reagents are de-contaminated by incubating the reagents in the presence of a nuclease and its co-factor (e.g., a metal ion). Suitable nucleases include, but are not limited to, exonucleases such as exonuclease I or exonuclease III. Proofreading DNA polymerases that may be used in a DNA amplification reaction may be de-contaminated by incubating with a divalent metal ion (e.g., magnesium or manganese). The free nucleotides employed in nucleic acid template amplification may include natural nucleotides (e.g., dATP, dGTP, dCTP, or dTTP) or their modified analogues. Other components such as buffers, salts and the like may also be added to allow the nucleic acid amplification to occur efficiently.

In some embodiments, kits for nucleic acid amplification are provided. The kits contain reagents, packaged together, that are required to practice the presently described methods of nucleic acid amplification. In one embodiment, the kit comprises a nucleic acid polymerase and a partially constrained primer having a terminal mismatch primer-dimer structure. The nucleic acid polymerase and the partially constrained primer may be packaged in a single vessel or they may be packaged in separate vessels.

In one embodiment, the kit comprises a Phi29 DNA polymerase and a partially constrained primer having a terminal mismatch primer-dimer structure, packaged together. The partially constrained primer in the kit may comprise a nucleotide analogue, such as a LNA nucleotide. In some embodiments, the partially constrained primer is a DNA-LNA chimera primer. The partially constrained primer in the kit may be a nuclease-resistant primer, for example, an exonuclease-resistant primer. These exonuclease-resistant primers in the kit may contain one or more phosphorothioate linkages between the nucleotides. In one embodiment, the kit comprises a partially constrained primer, the nucleotide sequence of which consists of W+W+NN*S, or W+W+NNN*S, and a Phi29 DNA polymerase.

The kit may further comprise reagents or reagent solutions required for performing a nucleic acid amplification reaction. It may further include an instruction manual detailing the specific components included in the kit, or the methods for using them in nucleic acid amplification reactions, or both.

EXAMPLES

Unless specified otherwise, ingredients described in the examples are commercially available from common chemical suppliers. Exonuclease I, Exonuclease III, 10×NE buffer, and EcoR1 enzyme are commercially available from New England Biolabs, MA. SYBR Green 1, Pico Green, and 1 Kb Plus DNA ladder are commercially available from Invitrogen. Single-Stranded Binding protein (SSB protein) is commercially available from USB. Some abbreviations used in the examples section are expanded as follows: "mg": milligrams; "ng": nanograms; "pg": picograms; "fg": femtograms; "ag": attograms; "zg": zeptograms; "mL": milliliters; "mg/mL": milligrams per milliliter; "mM": millimolar; "µM": micromolar; "pM": picomolar; "mmol": millimoles; "pmol": picomoles; "µL": microliters; "min.": minutes; "° C.": degree Celsius; and "h.": hours.

FIG. 1 is a schematic illustration of some possible primer-dimer structures that a partially constrained primer having a terminal mismatch primer-dimer structure may form during nucleic acid amplification reactions. The figure shows the primer-dimer structures of a partially constrained primer of the general formula $(W)_x(N)_y(S)_z$, wherein x=1, 2 or 3, y=3 and z=1 (a pentamer, a hexamer or a heptamer) according to one embodiment of the invention. The rectangular boxes in the figure represent the nucleotides having internal homology in the primer-dimer structure.

FIG. 1 shows that when two individual primer sequences in a partially constrained primer, $(W)_xN_3S$, wherein x=1, 2, or 3, consisting of n nucleotides (n is a variable number; e.g., for a hexamer primer, n=6) and having a terminal mismatch primer-dimer structure, hybridize each other inter-molecularly, with an internal homology of three or more nucleotides, to form a hybridization complex, either with no 3' recessed ends, or with (n-5)-nucleotide base long 3' recessed ends, there exist a nucleotide mismatch at both the 3' terminal nucleotides in the hybridization complex.

If a primer-dimer structure of a partially constrained pentamer primer having a sequence WNNNS is formed via inter-molecular hybridization, with no recessed ends, both the 3' terminal nucleotides will not be able to base pair (since W cannot base pair with S) in the primer-dimer structure. If such a hybridization event occurs during a nucleic acid amplification reaction conditions, a terminal mismatch primer-dimer structure is yielded. However, as shown in FIG. 1, if the primer WNNNS forms a primer-dimer structure with a single-nucleotide base 3' recessed ends, there may not be any terminal mismatch at both the 3' terminal nucleotides (i.e., S may base pair with N).

Similarly, if a partially constrained hexamer primer (n=6), having an oligonucleotide sequence WWNNNS, forms a primer-dimer structure with no recessed ends, both the 3' terminal nucleotides in the primer-dimer structure will not be able to base pair (since W cannot base pair with S). If such a hybridization event occurs, it will yield a terminal mismatch primer-dimer structure. Moreover, even if the primer WWNNNS forms a primer-dimer structure with a single-nucleotide base 3' recessed ends, terminal mismatch will exist at both the 3' terminal nucleotides in the primer-dimer structure. However, as illustrated in FIG. 1, the primer-dimer structures of WWNNNS having more than one-nucleotide base 3' recessed ends, will not have a terminal mismatch at the 3' terminal nucleotides.

A primer-dimer structures of a partially constrained heptamer primer WWWNNNS, host terminally mismatched 3' terminal nucleotides (unpaired 3' terminal nucleotides) in the primer-dimer structure if a primer-dimer structure is formed with no recessed ends, or with single-nucleotide base 3' recessed ends, or with two-nucleotide base 3' recessed ends (see. FIG. 1). However, the partially constrained heptamer primer, WWWNNNS will not have unpaired 3' terminal nucleotides if the primer-dimer structure formed by the inter-molecular hybridization has 3' recessed ends consisting of more than three nucleotides.

Example 1

The reagents and reagent solutions that were used for nucleic acid amplification reaction were de-contaminated in a nucleic acid-free hood prior to their use to remove any contaminating nucleic acids. The reagents such as Phi29 DNA polymerase, exonuclease I, exonuclease III, and SSB protein were stored in 50 mM Tris-HCl (pH 7.2), 200 mM NaCl, 10 mM DTT, 1 mM EDTA, 0.01% (v/v) Tween-20, and 50% (v/v) glycerol. The primer-nucleotide solution (primer-nucleotide mix) comprising primer and nucleotides (dNTPs) was de-contaminated by incubating the primer-nucleotide mix with a combination of exonuclease I, exonuclease III, and a single stranded DNA binding protein (SSB protein). The enzyme mix comprising a DNA polymerase was de-contaminated by incubating with an exonuclease in presence of a divalent cation (e.g., $Mg^{2+}$). Any target nucleic acid amplification reaction was performed using the de-contaminated enzyme mix and the primer-nucleotide mix.

As shown in Table 2, the enzyme mix containing 200 ng of Phi29 DNA polymerase was incubated with 0.1 unit of exonuclease III in 50 mM HEPES buffer (pH=8.0) containing 15 mM KCl, 20 mM $MgCl_2$, 0.01% (v/v) Tween-20, and 1 mM TCEP (Total volume was 5 µL). The incubation was performed either at 30° C. for about 60 min., or at 4° C. for 12 h. The incubated enzyme mix was then transferred to an ice-bath, and was used in DNA amplification reactions as such without any inactivation of the exonuclease III. This small amount of exonuclease III had no substantial effect on the amplification reaction if the finished amplification reaction was treated immediately upon completion to inactivate the exonuclease.

To de-contaminate the primer-nucleotide mix, it was incubated with a combination of exonuclease I, exonuclease III and SSB protein as shown in Table 1. The incubation was performed at 37° C. for about 60 min. in 50 mM HEPES buffer (pH=8.0) containing 15 mM KCl, 20 mM $MgCl_2$, 0.01% (v/v) Tween-20 and 1 mM TCEP (Total reaction volume was 5 µL). *E. Coli* SSB protein was used in this example as a suitable single-stranded binding protein. After decontamination of the primer-nucleotide mix, the exonucleases were thermally inactivated by incubating the primer-nucleotide mix at 85° C. for about 15 min., followed by incubation at 95° C. for about 5 min to about 10 min.

For nucleic acid amplification reaction, the primer-nucleotide mix and the enzyme mix was mixed together along with template nucleic acid to create an amplification reaction, which was then incubated at about 30° C. The time at which the signal in each reaction reached a specific minimal fluorescent intensity was identified.

For reactions with rapid kinetics, the signal appears more quickly; and for reactions with slower kinetics (such as those with lower levels of input template DNA), the signal appears more slowly. In these reactions, and specific for each reaction, there is a relationship between the amount of DNA template used and the time at which the signal appears. Additionally, the time required for signal to appear in reactions that contain no input template DNA is an indication of how efficiently the reaction can produce an artificial template by some de-novo process, and then amplify the artificial template (non-specific amplification). Reaction modifications that retain rapid kinetics in the presence of template DNA, yet slow kinetics of reactions that lack template DNA are desirable.

TABLE 2

De-contamination of the enzyme mix and primer-nucleotide mix solutions.

| | Primer-nucleotide mix (each reaction) | DNA polymerase (enzyme) mix (each reaction) |
|---|---|---|
| 2X Reaction buffer (reaction buffer is 50 mM HEPES buffer (pH = 8.0), 15 mM KCl, 20 mM MgCl$_2$, 0.01% Tween-20 and 1 mM TCEP) | 2.5 µL | 2.5 µL |
| Distilled water | — | 2.2 µL |
| 10 mM dNTP mix | 0.4 µL | — |
| 1 mM primer | 0.4 µL | — |
| Exonuclease I (20 unit/µL) | 0.5 µL | — |
| Exonuclease III (10 unit/µL) | 0.1 µL | — |
| Exonuclease III (1 unit/µL) | — | 0.1 µL |
| SSB protein (100 ng/µL) | 1 µL | — |
| 1:100 SYBR Green I | 0.1 µL | — |
| Phi29 DNA polymerase (1 mg/ml) | — | 0.2 µL |
| Total reaction volume | 5 µL | 5 µL |

Example 2

Non-specific amplification reaction during a nucleic acid amplification reaction was estimated by performing a DNA amplification reaction without any added template DNA (No Template Control (NTC) amplification). The reactions employed either a completely random hexamer primer (NNNN*N*N), or a partially constrained pentamer primer (W+W+N*N*S) that comprises LNA nucleotides, which has a terminal mismatch primer-dimer structure. Both these primers were exonuclease-resistant primers, having phosphorothioate linkages between the nucleotides toward the 3' end of the sequence.

The amplification products from a DNA amplification reaction with no added target DNA template (NTC) arise from non-specific amplification reactions (false amplification or background amplification). The non-specific amplification may be due to amplification of contaminating DNA molecules, or it may be due to primer gymnastics (e.g., formation of primer-dimer structures, and subsequent extension of primer-dimers). To avoid any non-specific amplification reaction originating from contaminating DNA, all the reagents or reagent solutions (enzyme mix and primer-nucleotide) that were used for the amplification reaction were de-contaminated to remove any contaminating DNA using the procedure described in Example 1.

For estimating non-specific DNA amplification reactions, DNA amplification reaction was performed by incubating the de-contaminated primer-nucleotide mix and the de-contaminated enzyme mix at 30° C. for about 400 min without any added DNA template. The amplification reaction mixture was composed of 40 µM primer (random hexamer, NNNN*N*N, or partially constrained pentamer, W+W+N*N*S); 400 µM dNTPs (equal mixture of each of dATP, dCTP, dGTP, dTTP); and 0.3 µM phi29 DNA polymerase (200 ng per 10 µL reaction). The incubation was performed in 50 mM HEPES buffer (pH=8.0) containing 15 mM KCl, 20 mM MgCl$_2$, 0.01% (v/v) Tween-20, 1 mM TCEP, and 1:10,000 (v/v) SYBR Green I. Real-time data was collected in Tecan fluorescent plate reader by monitoring the SYBR Green fluorescence using an excitation wavelength of 485 nm and an emission wavelength of 535 nm.

The time at which the fluorescent signal in each reaction has reached a specific minimal fluorescent intensity is graphically represented in FIG. 2. The time required for fluorescent signal to appear in reactions that contain no input template DNA is an indication of how efficiently the reaction can produce an artificial template by some de-novo process and then amplify the artificial template (non-specific amplification reaction).

FIG. 2 shows that the partially constrained pentamer primer comprising LNA nucleotides (W+W+N*N*S) decreased the non-template amplification kinetics. When the amplification reaction employed the random hexamer primer, NNNN*N*N, DNA amplification products (non-specific amplification products) were observed at about 200 min. In contrast, when partially constrained pentamer primer W+W+N*N*S was used for the amplification reaction, the non-specific amplification products appeared only after about 300 min. This illustrates that DNA amplification at zero target DNA concentration (the false amplification products) was considerably reduced when partially constrained primer having a terminal mismatch primer-dimer structure was employed.

Since all the reagents were de-contaminated prior to DNA amplification reaction, significant contribution toward non-specific amplification originates from primer gymnastics under amplification reaction conditions. Hence, reduction of non-specific amplification products indicates reduced primer gymnastics. Multiple factors may contribute to the reduction of primer-primer interaction in a partially constrained primer having terminal mismatch primer-dimer structure. The reduction of the length of the primer from a hexamer to a pentamer reduces the possibility of formation of stable primer-dimer structures under nucleic acid amplification reaction conditions. Moreover, the partially constrained W+W+N*N*S, when hybridized inter-molecularly with no recessed ends or with a single nucleotide 3' recessed ends, hosts a terminal mismatch primer dimer structure. Such primer-dimer structures, if formed, will have 3' terminal nucleotides that are not base-paired. Hence, formation of such primer-dimer structures may be limited. Furthermore, incorporation of LNA nucleotides in the partially constrained pentamer primer increases the binding specificity of the primer to the complementary sequences. Higher specificity primers comprising LNA nucleotides allow the amplification reaction to be performed at lower salt concentration of about 15 mM to about 20 mM (high stringent hybridization conditions) as compared to the commonly used salt concentration of about 75 mM. In this example, the amplification reactions were performed at a lower salt concentration of about 15 mM salt. The reduction in salt concentration results in higher stringency hybridization conditions so that the chances of formation of stable primer-dimer structures under the amplification reaction conditions are further reduced. Moreover, since the partially constrained primer has a terminal mismatch primer-dimer structure, even if primer-dimer structures were formed, primer dimer extension reactions would not have been possible due to mismatched 3' terminal nucleotides.

Example 3

Higher specificities of DNA amplification with a partially constrained primer is illustrated by performing DNA amplification reactions at varying concentrations of target DNA template. To avoid any non-specific amplification reaction from contaminating DNA, all reagents or reagent solutions (enzyme mix and primer-nucleotide mix) that were used for the amplification reaction were de-contaminated prior to their use following the procedure described in Example 1. The de-contaminated enzyme mix and primer-nucleotide mix were then combined to form a reaction mixture, which was comprised of 40 µM primer (either a random hexamer, NNNN*N*N, or a partially constrained pentamer primer, W+W+N*N*S), 400 µM dNTPs (equal mixture of each of dATP, dCTP, dGTP, dTTP), and 0.3 µM phi29 DNA polymerase (200 ng per 10 µL reaction) in 50 mM HEPES buffer (pH=8.0) containing 15 mM KCl, 20 mM MgCl2, 0.01% (v/v) Tween-20, 1 mM TCEP, and 1:10,000 (v/v) SYBR Green I. The reaction mixture also contained 0.1 unit exonuclease III, 1 unit of exonuclease III (heat-inactivated), 10 units of exonuclease I (heat-inactivated) and 100 ng E. coli SSB protein (heat-inactivated) from the de-contamination procedure.

Combined enzyme mix and primer-nucleotide mix were placed in low-binding PCR tubes on ice (12 tubes, each having 10 µL reaction mixture). Serial dilutions of a plasmid DNA were performed so as to have varying numbers of plasmid DNA molecules in each of the PCR tubes. Briefly, 1 µL of 1 ng/µL pUC19 plasmid (about $3\times10^8$ DNA circles) was added to the first tube. The reaction mixture was mixed well, and 1 µL was transferred from the first tube to the second tube to achieve a 10-fold serial dilution (i.e., about $3\times10^7$ DNA circles). This process was repeated from tube 2 to tube 3 and continued till tube 11. In the $12^{th}$ tube, no template DNA was added and thus served as no template control (NTC).

For DNA amplification, from each tube, 10 µL reaction mixture was transferred to a 384-well, flat bottom plate (384 Black from BD Falcon Microtest) with a transparent cover. It was then incubated in SniPer (Tecan) at about 30° C. The parameters used were; Gain: Manual-40; Lag time: 0 µs; Z-position: Manual-8700; Integration time: 40 µs; #Flash: 10 ms; Time between move: 0 ms; cycles: 50, 00:10:00 each. Real-time data was collected in Tecan fluorescent plate reader by monitoring the SYBR Green fluorescence using an excitation wavelength of 485 nm and an emission wavelength of 535 nm.

Figure 3:
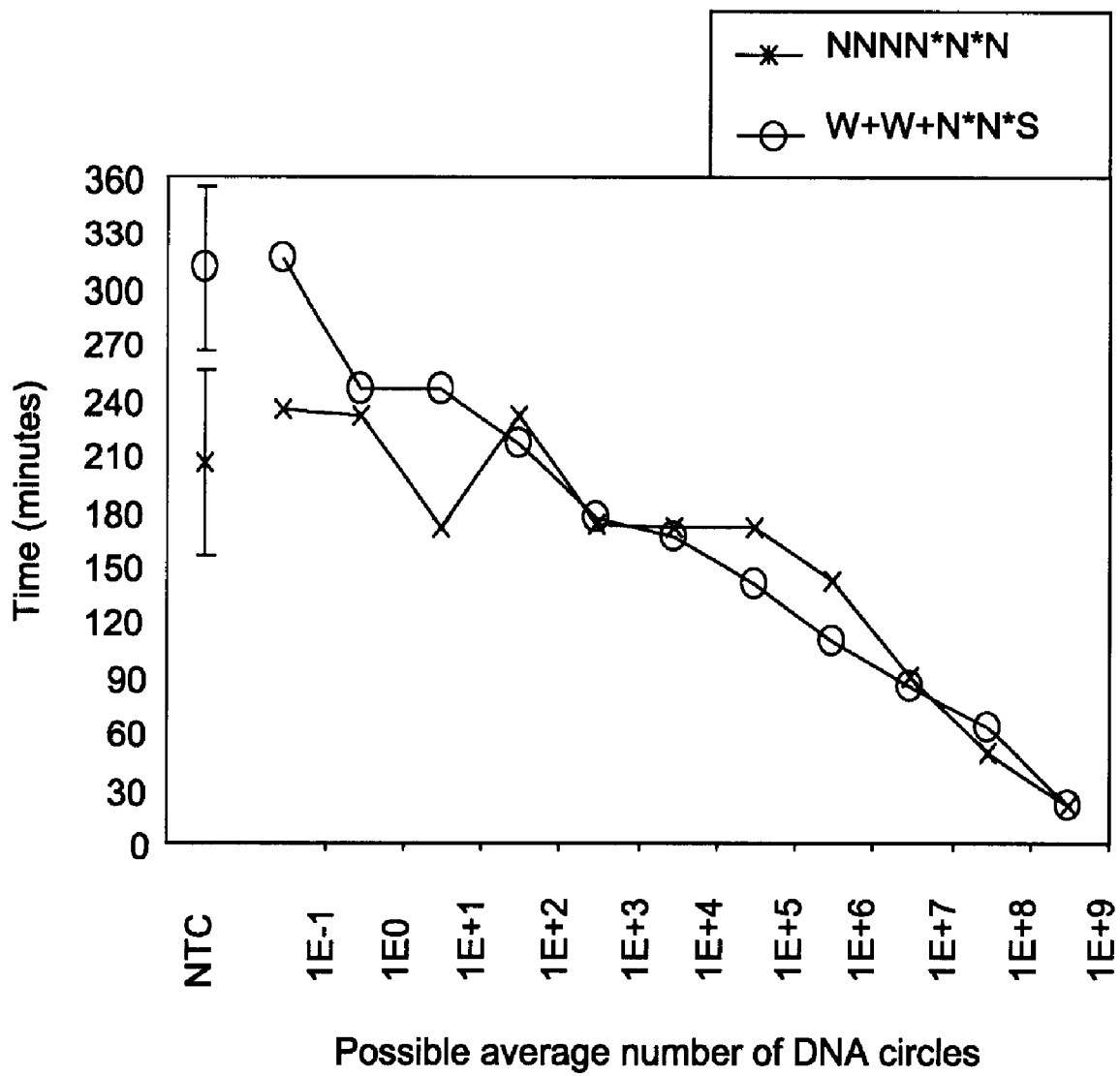
FIG. 3 shows higher amplification specificities of a DNA amplification reaction when a partially constrained primer according to one embodiment of the invention is used in the DNA amplification reaction.

FIG. 3 shows the higher amplification efficiencies of the DNA amplification reaction when the partially constrained primer, W+W+N*N*S was used in the DNA amplification reaction. The figure shows that the no-template amplification (NTC) was reduced considerably in the reaction employing W+W+N*N*S in comparison with the reaction employing the random primer, NNNN*N*S. The reduction in no-template amplification (back ground, non-specific amplification) may be attributed to the reduction in the formation of stable primer-dimer structure when the partially constrained primer, W+W+N*N*S having terminal mismatch primer-dimer structure was used for DNA amplification. Moreover, even if the primer-dimer structure were formed when using W+W+N*N*S (either with no recessed 3' ends or with a single nucleotide length 3' recessed ends), due to 3' terminal nucleotide mismatch, no primer extension reactions would have been possible during DNA amplification. This is in contrast the usage of NNNN*N*S, wherein formation of primer-dimer structures and their extensions are possible during DNA amplification reaction conditions.

FIG. 3 also illustrates that the DNA amplification efficiencies of the partially constrained primer, W+W+N*N*S, was comparable to that of random primer, NNNN*N*S when the average number of target DNA circles was above $1\times10^0$ DNA circles. This illustrates that W+W+N*N*S is efficient in reducing non-specific amplification reactions (average number of DNA circles below $1\times10^0$) and so may be effectively used for single molecule DNA amplification.

Example 4

Efficiency of a partially constrained primer for use in single molecule DNA amplification was demonstrated by amplification of a mixture of plasmids, pUC19 and pGEM-3Z-f(−). By diluting the mixture of plasmids, one should eventually reach a concentration at which the reaction mixture shall have only one of the two plasmids. Thus, by serially diluting the plasmid mixture, the dilution (or concentration) at which the amplification of only a single plasmid of the plasmid mixture occurs was identified.

To avoid any non-specific amplification reaction from contaminating DNA, all reagents or reagent solutions (enzyme mix and primer-nucleotide) that were used for the amplification reaction were de-contaminated prior to their use following the procedure described in Example 1. The de-contaminated enzyme mix and primer-nucleotide mix were then combined to form a reaction mixture (total volume 10 µL), which was comprised of 40 µM primer (either a random hexamer, NNNN*N*N or a partially constrained pentamer, W+W+N*N*S), 400 µM dNTPs (equal mixture of each of dATP, dCTP, dGTP, dTTP), and 0.3 µM phi29 DNA polymerase (200 ng per 10 µL reaction) in 50 mM HEPES buffer (pH=8.0) containing 15 mM KCl, 20 mM MgCl2, 0.01% (v/v) Tween-20, 1 mM TCEP, and 1:10,000 (v/v) SYBR Green I. The reaction mixture also contained 0.1 unit exonuclease III, 1 unit of exonuclease III (heat-inactivated), 10 units of exonuclease I (heat-inactivated) and 100 ng E. coli SSB protein (heat-inactivated) from the de-contamination procedure.

The reaction mixture (combined enzyme mix and primer-nucleotide mix) was placed in low-binding PCR tubes on ice (12 tubes, each having 10 µL reaction mixture). Serial dilutions of a mixture of plasmid DNAs (pUC19 and pGEM-3Z-f(−)) were performed in the reaction mixture so as to have varying numbers of plasmid DNA molecules in each of the PCR tubes. Briefly, 1 µL of 1 ng/µL pUC19 plasmid and pGEM-3Z-f(−) plasmid mixture (1 ng plasmid DNA is about $3\times10^8$ DNA circles) was added to the first tube. The reaction mixture was mixed well, and 1 µL from the first tube was transferred to the second tube to achieve a 10-fold serial dilution. The second tube will then have about $3\times10^7$ DNA circles. This process was repeated from tube 2 to tube 3, and continued till tube 11. Predicted average number of DNA molecules that each tube may contain due to serial dilution is illustrated in Table 3. In the $12^{th}$ tube, no template DNA was added and thus served as no template control (NTC).

TABLE 3

Concentration and predicted number of DNA molecules upon 10-fold serial dilutions.

| Tube Number | Concentration of DNA | Predicted avarge number of DNA molecules |
| --- | --- | --- |
| 1 | 1 ng | $3 \times 10^8$ |
| 2 | 100 pg | $3 \times 10^7$ |
| 3 | 10 pg | $3 \times 10^6$ |
| 4 | 1 pg | $3 \times 10^5$ |
| 5 | 100 fg | $3 \times 10^4$ |
| 6 | 10 fg | $3 \times 10^3$ |
| 7 | 1 fg | $3 \times 10^2$ |
| 8 | 100 ag | $3 \times 10^1$ |

TABLE 3-continued

Concentration and predicted number of DNA molecules upon 10-fold serial dilutions.

| Tube Number | Concentration of DNA | Predicted avarge number of DNA molecules |
|---|---|---|
| 9 | 10 ag | $3 \times 10^{0}$ |
| 10 | 1 ag | $3 \times 10^{-1}$ |
| 11 | 100 ag | $3 \times 10^{-2}$ |
| 12 | 0 | 0 (No Template Control) |

For DNA amplification, 10 μL reaction mixture from each tube was transferred to a 384-well, flat bottom plate (384 Black from BD Falcon Microtest) having a transparent cover. It was then incubated in SniPer (Tecan) at about 30° C. The parameters used were; Gain: Manual-40; Lag time: 0 μs; Z-position: Manual-8700; Integration time: 40 μs; #Flash: 10 ms; Time between move: 0 ms; and cycles: 50, 00:10:00 each. Real-time data was collected in Tecan fluorescent plate reader by monitoring the SYBR Green fluorescence using an excitation wavelength of 485 nm and an emission wavelength of 535 nm.

Following the amplification, the plate was spun down in a centrifuge, and the samples were transferred to 0.2 mL PCR strip tubes. Phi29 DNA polymerase in the reaction mixture was denatured by incubating the tubes at about 80° C. for about 30 min. The tubes were then cooled to room temperature by keeping them at room temperature for about 30 min.

The amplification products in each tube were restriction digested using EcoR1 enzyme. Briefly, 2 μL of amplified product was mixed with 1 μL of EcoR1 (10 Units/μL), 1 μL 10×NE buffer, and 6 μL distilled water (total volume of 10 μL). The mixture was incubated at 37° C. for 1 h. The digested products in each tube was mixed with 3 μL of loading dye (2 μL 6× loading buffer+1 μL 1:200 PicoGreen) and loaded in 0.8% agarose gel. 1 Kb Plus DNA Ladder was used in the marker lane (9 μL TE buffer, 2 μL 6× loading buffer, 1 μL 1:200 PicoGreen and 1 μL of 1 Kb Plus DNA Ladder (1 μg/μL) were mixed together and loaded 10 μL on the gel).

Figure 4:
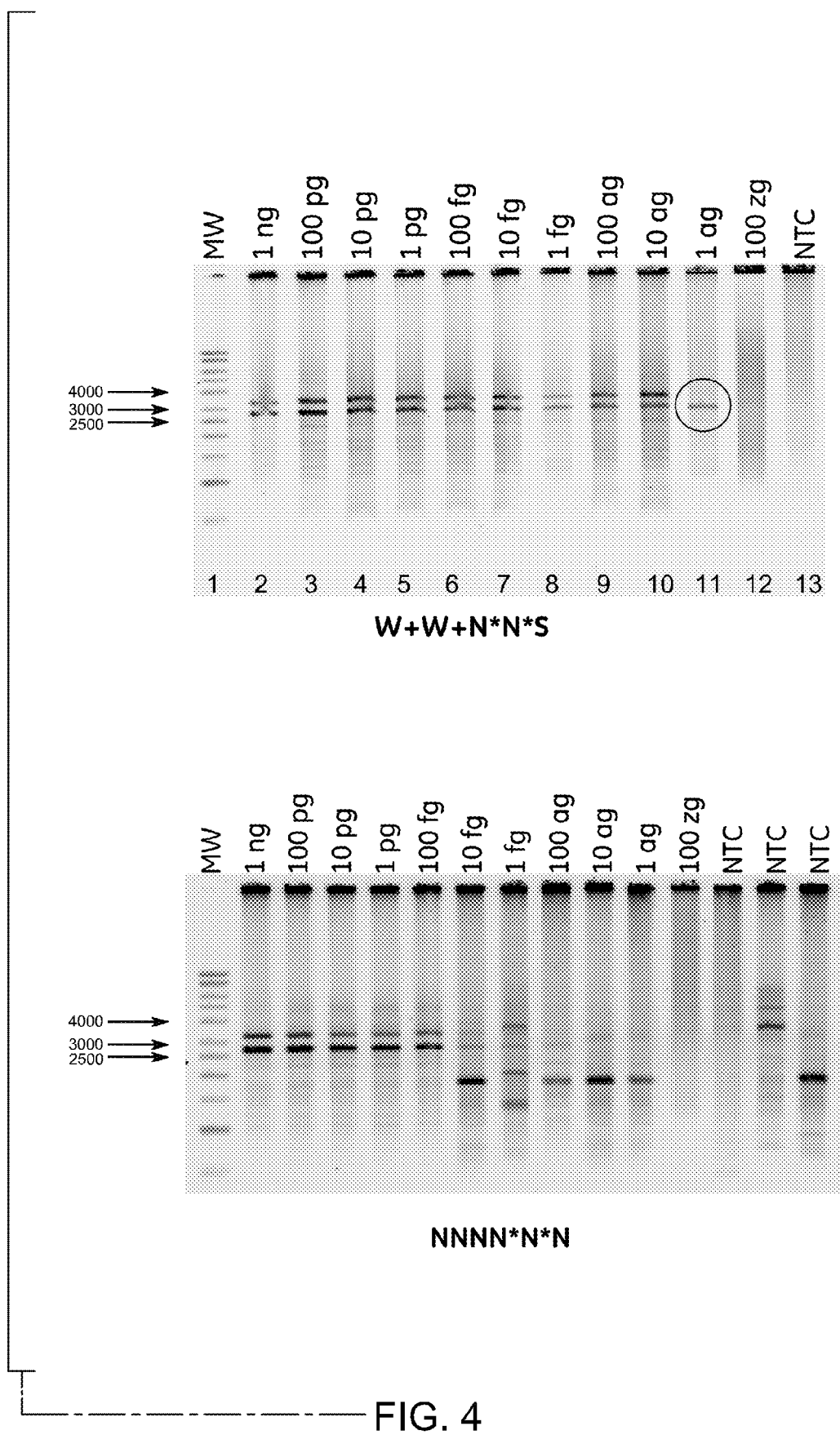
FIG. 4 shows single DNA molecule amplification using a partially constrained primer having a terminal mismatch primer-dimer structure according to one embodiment of the invention.

FIG. 4 shows the agarose gel of the EcoR1 restriction digest of amplification products of mixtures of pUC19 (2686 base pairs) and pGEM-3Z-f(-) (3197 base pairs). By diluting the mixture of plasmids, one will eventually reach a concentration at which the reaction mixture will have only one of the two plasmids. It can be seen from FIG. 4 that when partially constrained primer, W+W+N*N*S was used for amplification, amplification products were obtained from reaction mixtures that seemingly had only one of the two plasmids in it (Lane 11: amplification from 1 ag of DNA). Lane 11 shows the amplification products from pUC19 (circled) and does not show any amplification products that correspond to pGEM DNA. This indicates that at this dilution, the reaction mixture had only pUC19 DNA and did not contain any pGEM DNA. In contrast, the random hexamer primer, NNNN*N*S did not facilitate amplification from single/few DNA molecules. Amplification reactions employing NNNN*N*S did not have enough sensitivity to reach that level and specific products were no longer made below the 1000 DNA molecule level. This indicates that the partially constrained primer, W+W+N*N*S having a terminal mismatch primer-dimer structure was more efficient in amplification reactions having smaller amount of target template DNA.

Figure 5:
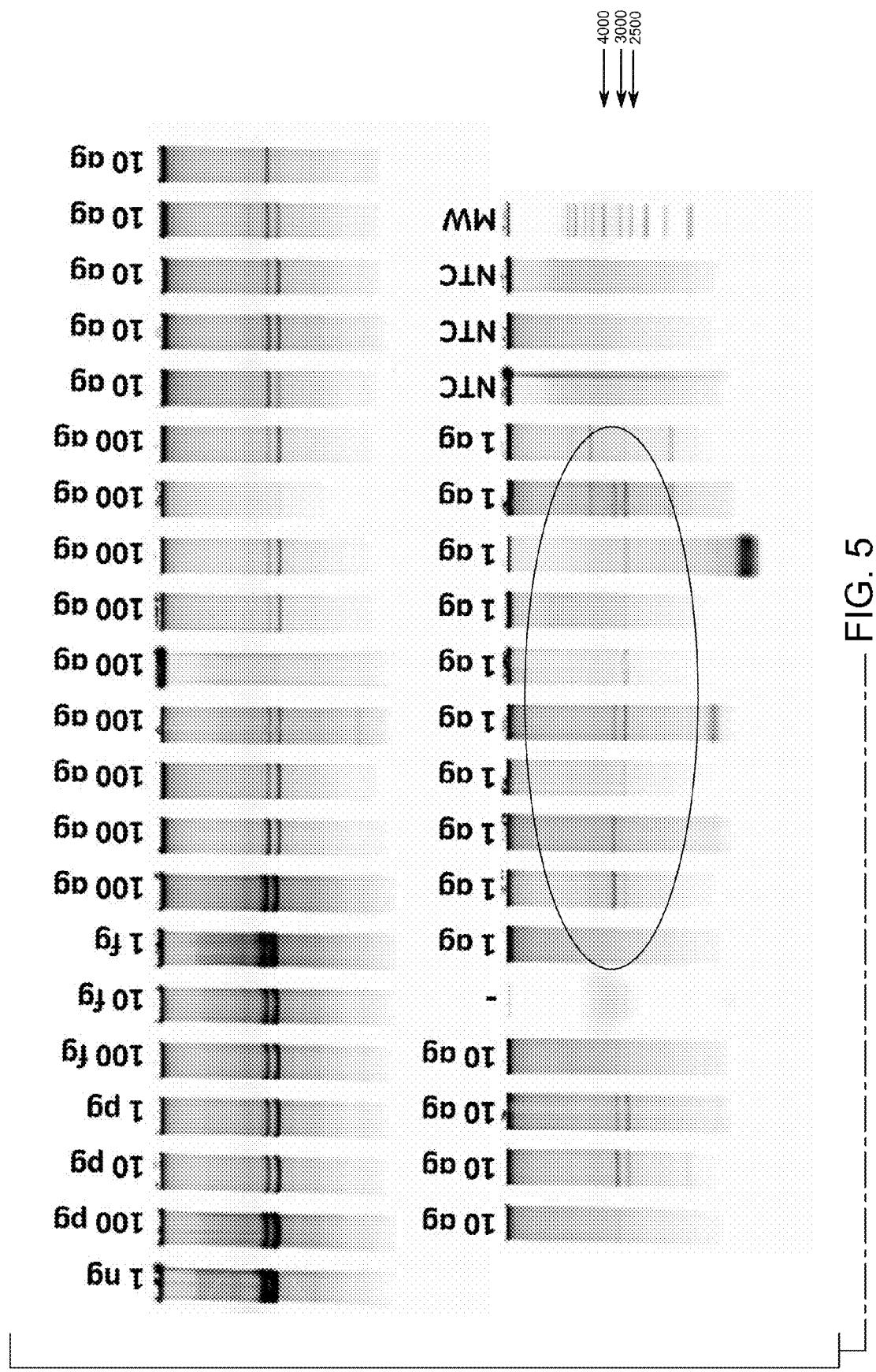
FIG. 5 shows the stochastic nature of DNA amplification products when a partially constrained primer having a terminal mismatch primer-dimer structure according to one embodiment of the invention is used in a single DNA molecule amplification reaction.

FIG. 5 demonstrates the stochastic nature of single molecule DNA amplification when W+W+N*N*S was employed in the amplification reaction. As shown in FIG. 4, by serially diluting the plasmid mixture, it was possible to find out a dilution at which only one of the plasmids in the plasmid mixture got amplified (e.g., DNA concentration of 1 ag). However, when multiple, independent DNA amplification reactions were performed at such dilutions, the amplification reactions were found to be stochastic. Few of the amplification reactions using 1 ag of template DNA circles amplified both the plasmids, some amplified only pGEM-3Z-f(-), whereas some others amplified only pUC19. Some amplification reactions did not amplify any of the two plasmids, and showed non-specific amplification reactions (background amplifications).

Example 5

Amplification efficiencies of a partially constrained primer that consist of only one phosphorothioate linkage between a 3' terminal nucleotide and a nucleotide that is adjacent to the 3' terminal nucleotide is compared with that of a partially constrained primer consisting of multiple phosphorothioate linkages.

DNA amplification reactions at varying concentration of a mixture of plasmids, pUC19 and pGEM-3Z-f(-) were performed using primers W+W+N*N*S or W+W+NN*S. To avoid any non-specific amplification reaction from contaminating DNA, all reagents or reagent solutions (enzyme mix and primer-nucleotide) that were used for the amplification reaction were de-contaminated prior to their use following the procedure described in Example 1. The procedure used for DNA amplification reaction and subsequent restriction digestion were essentially the same as described in Example 4. By diluting the mixture of plasmids, one should eventually reach a concentration at which the reaction mixture shall have only one of the two plasmids.

When a reaction to form a phosphorothioate linkage between two nucleotides is performed, only about 50% the nucleotide linkages will actually be exonuclease-resistant. This is due to the fact that in a phosphorothioation reaction only 50% of the linkages are eventually phosphorothioated, making them exonuclease resistant. Hence, when a partially constrained primer is designed to contain two phosphorothioate bonds (e.g., W+W+N*N*S), during its chemical synthesis, some of the primer sequences (in the partially constrained mixture of sequences) may actually end up with having only one phosphorothioate linkage instead of the designed two (e.g., W+W+NN*S or W+W+N*NS). Hence, there exists a possibility that some of the sequences may have a terminal 3' nucleotide, having a linkage that is exonuclease sensitive (e.g., W+W+N*NS). Under such situation, the de-contamination procedures as described in Example 1, may remove the 3' terminal nucleotide of W+W+N*NS and may yield a partially constrained primer that has completely randomized 3' terminal nucleotide (W+W+N*N). The tetramer product, W+W+N*N then support primer-dimer structures having no terminal mismatch and may support extension reactions from its primer-dimer structures. However, a partially constrained primer having a sequence W+W+NN*S, will not generate such unwanted sequences in the reaction mixture. During the chemical synthesis of W+W+NN*S, some sequences may be generated having a sequence W+W+NNS. However, such exonuclease-sensitive sequences will be completely digested during the de-contamination procedure. Hence, a partially constrained primer consisting of a single phosphorothioate linkage does not generate unwanted sequences during de-contamination procedures, and so was expected to reduce non-specific amplification reaction considerably.

Figure 6:
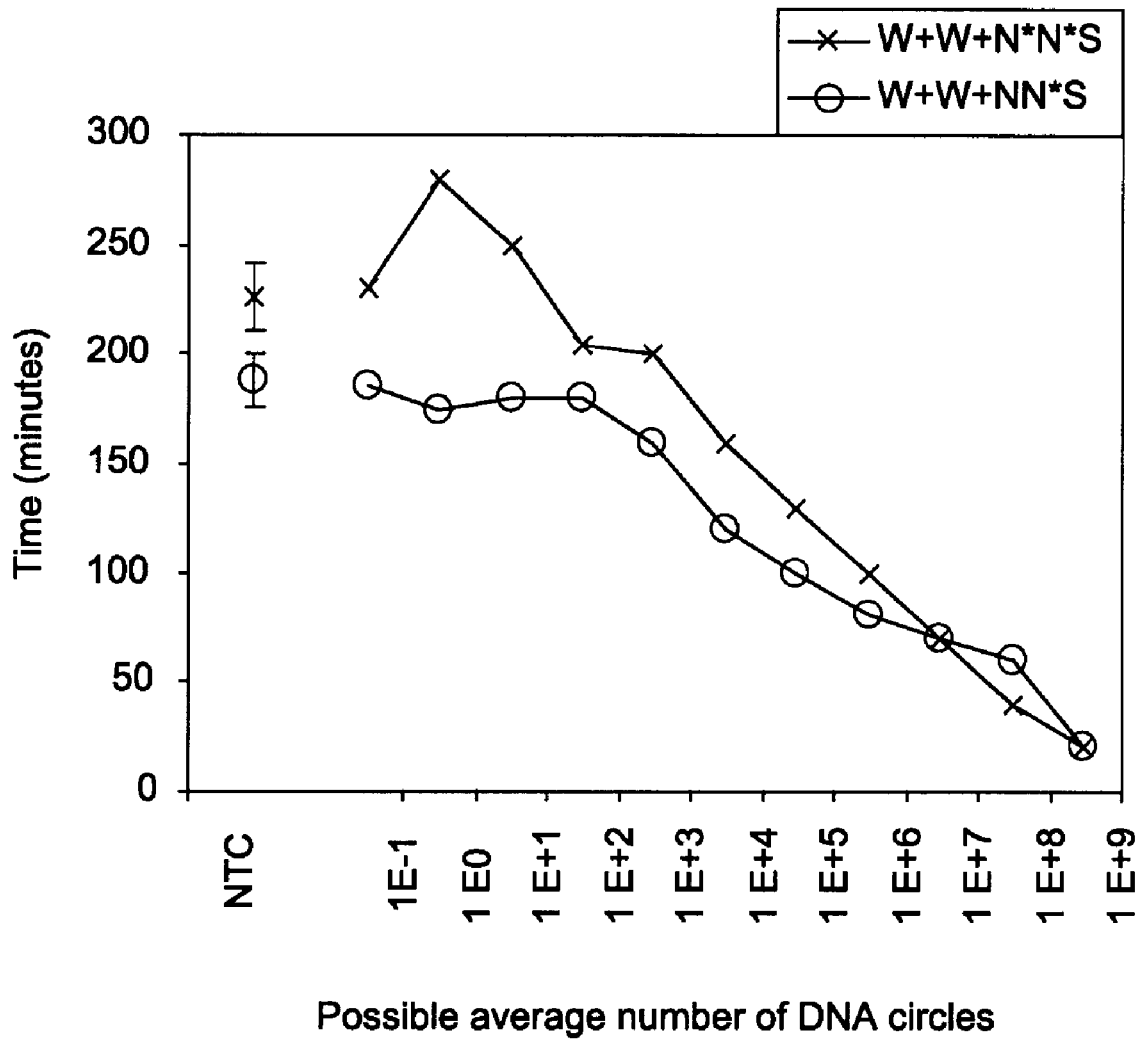
FIG. 6 shows the amplification kinetics of various nuclease-resistant, partially constrained primers having terminal mismatch primer-dimer structures. The partially constrained primers contain varying number of phosphorothioate linkages.
Figure 7:
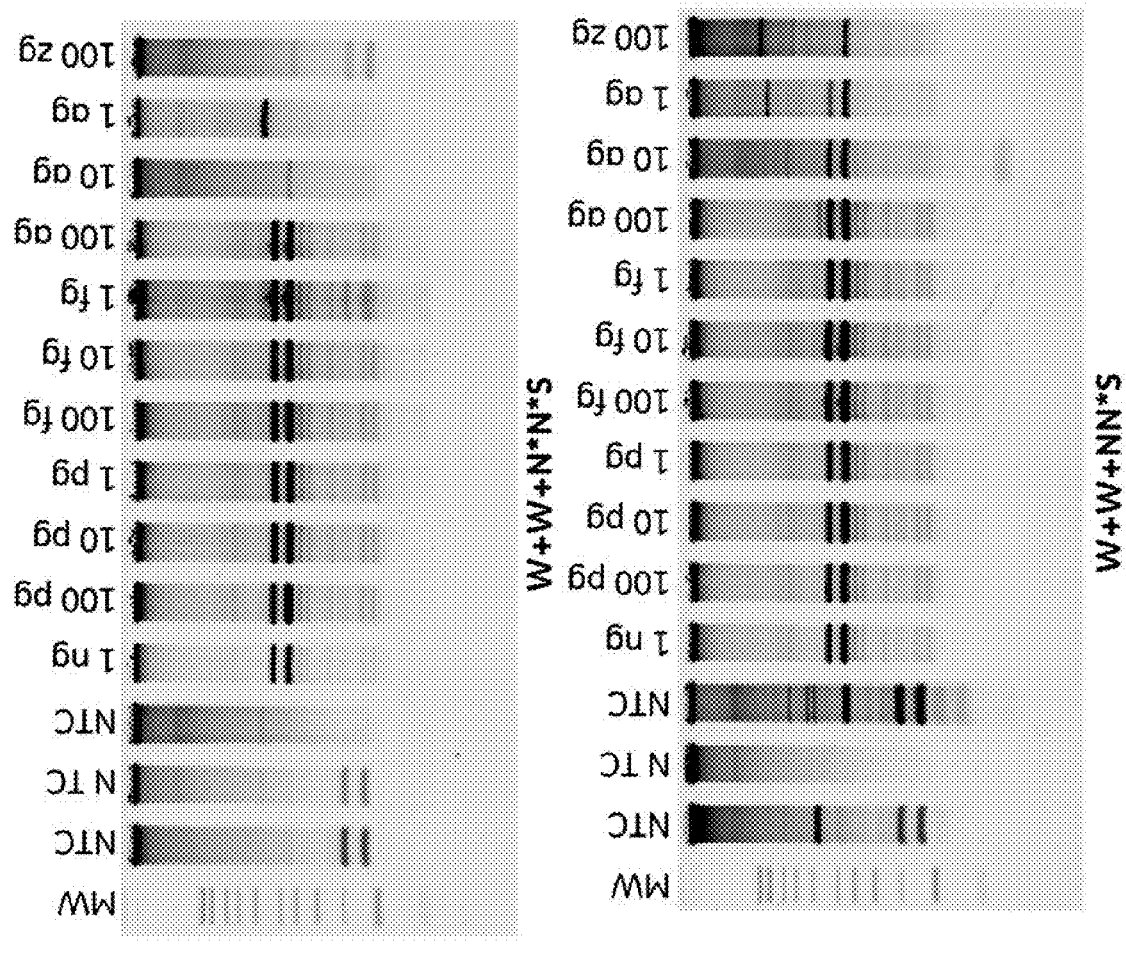
FIG. 7 shows the restriction digestion pattern of the amplification products when various nuclease-resistant partially constrained primers having terminal mismatch primer-dimer structures were used for nucleic acid amplification. The partially constrained primers contain varying number of phosphorothioate linkages.

However, as shown in FIG. 6 and FIG. 7, non-specific amplification reactions were not reduced when a partially constrained primer that consists of only one phosphorothioate linkage between a 3' terminal nucleotide and a nucleotide that is adjacent to the 3' terminal nucleotide (W+W+NN*S) was employed for DNA amplification reactions. No template amplification (NTC) surfaced at about 175 min. when W+W+ NN*S was used. However, when W+W+N*N*S was used for DNA amplification, no template amplification was observed only after about 230 min.

FIG. 7 shows that non-specific amplification was more when W+W+NN*S was employed in a nucleic acid amplification with 1 ag template DNA.

Example 6

Nucleic acid amplification efficiencies of various exonuclease-resistant primers (random primer or partially constrained primers) comprising nucleotide analogues were estimated by comparing their DNA amplification efficiencies with or without added template DNA. To avoid any non-specific amplification reaction from contaminating DNA, all reagents or reagent solutions (enzyme mix and primer-nucleotide) that were used for the amplification reaction were de-contaminated prior to their use following the procedure described in Example 1.

DNA amplification reactions were performed following the procedures provided in previous examples. For estimating non-specific DNA amplification reactions, DNA amplification reactions were performed without adding any template DNA (no template control). For amplification reactions containing a target DNA template, 0.5 pg of pUC19 plasmid DNA was used as a suitable template.

The amplification reaction mixture was composed of 40 µM primer; 400 µM dNTPs (equal mixture of each of dATP, dCTP, dGTP, dTTP); and 0.3 µM phi29 DNA polymerase (200 ng per 10 µL reaction) in 50 mM HEPES buffer (pH=8.0) containing 15 mM KCl, 20 mM MgCl2, 0.01% (v/v) Tween-20, 1 mM TCEP, and 1:10,000 (v/v) SYBR Green I. The DNA amplification was performed by incubating the reaction mixture (with or without added template DNA) at about 30° C. for about 400 min. Real-time data was collected in Tecan fluorescent plate reader by monitoring the SYBR Green fluorescence using an excitation wavelength of 485 nm and an emission wavelength of 535 nm.

Figure 8:
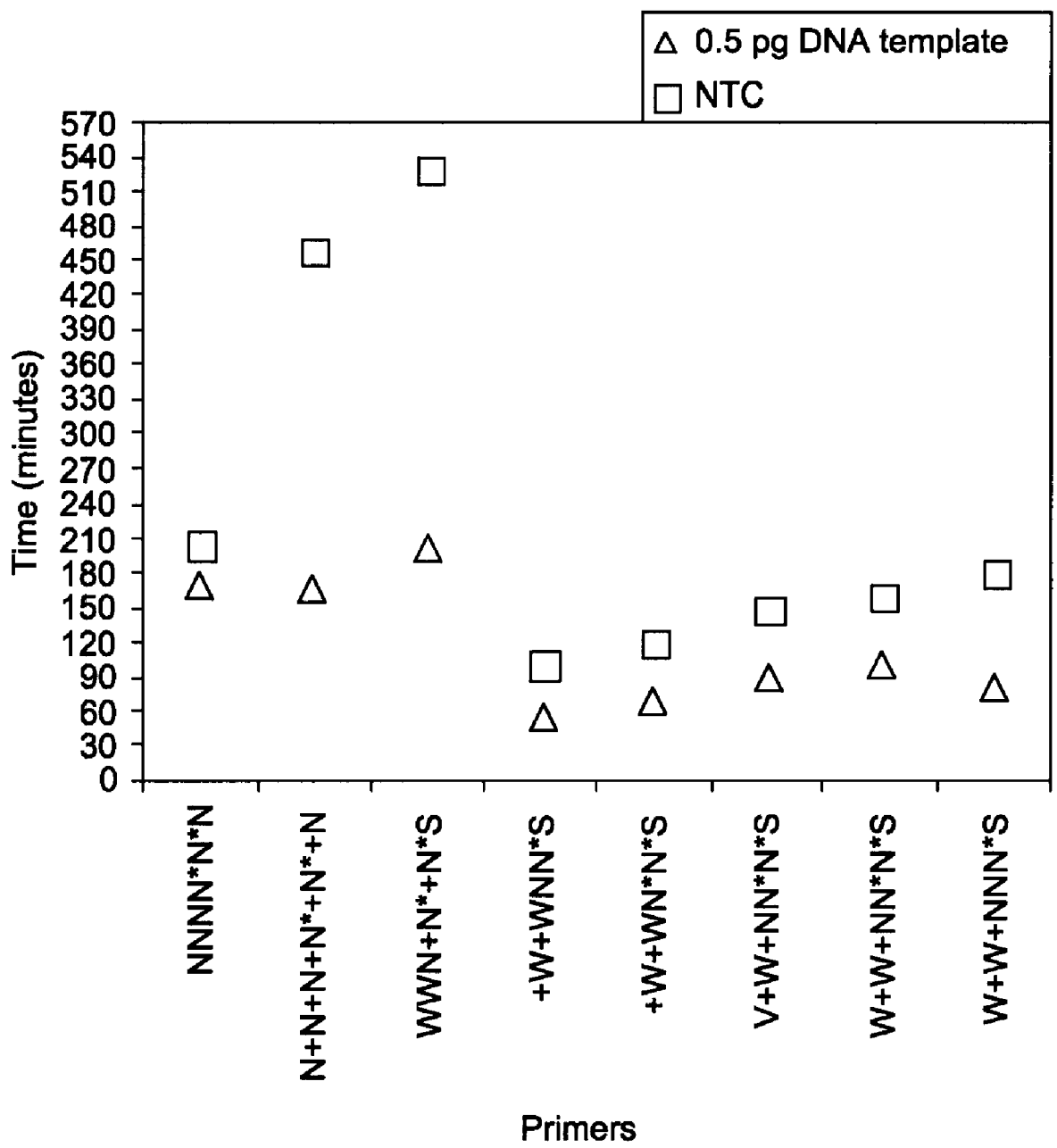
FIG. 8 shows amplification efficiencies of various primers that comprise nucleotide analogues in a DNA amplification reaction according to some embodiments of the invention.

The time at which the signal in each reaction reached a specific minimal fluorescence intensity is identified, and is shown in FIG. 8. For reactions with rapid kinetics, the signal appears more quickly; and for reactions with slower kinetics the signal appears more slowly. Additionally, the time required for the signal to appear in reactions that contain no input template DNA is an indication of how efficiently the reaction can produce an artificial template by some de-novo process and then amplify the artificial template (non-specific amplification). Reaction modifications that retain rapid kinetics in the presence of template DNA, yet slow kinetics of reactions that lack template DNA, are desirable.

FIG. 8 shows the amplification kinetics of DNA amplification reactions with different primers. In amplification reactions employing a random primer, NNN*N+N the fluorescent signal from non-template control appeared almost at the same time as that of amplification reaction having 0.5 pg of template DNA. This indicates that the reaction kinetics in the presence of 0.5 pg of template DNA is almost the same as that of reaction lacking template DNA. When primers such as N+N+N+N*+N, or WWN+N*+N*S, wherein LNA nucleotides were located toward 3' ends, were used for amplification reaction, the no template amplification kinetics were significantly slower. The fluorescent signals were visible only after about 450 min. of the reaction. However, these primers also reduced the kinetics of the amplification reaction even with 0.5 pg of template DNA (The fluorescent signals appeared only after about 150 min. of reaction). Primers wherein the LNA nucleotides were positioned toward the 5' end of the primer sequence (e.g., +W+WNN*S, +W+WN*N*S, V+W+NN*N*S, W+W+NN*N*S, or W+W+NNN*S), demonstrated significantly better amplification efficiencies. These primers slowed down the kinetics of the no template reaction without significantly slowing down the kinetics of amplification reaction in the presence of template DNA.

Example 7

DNA amplification efficiencies of some partially constrained primers having terminal mismatch primer-dimer structures are illustrated by performing DNA amplification reactions at varying concentrations of target template DNA. To avoid any non-specific amplification reactions as a result of contaminating DNA, all reagents or reagent solutions (enzyme mix and primer-nucleotide) that were used for the amplification reaction were de-contaminated prior to their use following the procedure described in Example 1.

Varying concentrations of pUC19 plasmid DNA (0 g (NTC), 25 pg, 250 fg, 2.5 fg, 25 ag, or 250 zg) were placed in low binding PCR tubes. The tube without added pUC19 DNA served as no template control (NTC). DNA amplification reactions were performed using each of the primers following the amplification procedures described in previous examples. Briefly, each of the amplification reactions contained, apart from the target DNA, 40 µM partially constrained primer (W+W+NN*N*S, V+W+N*N*S or W+W+N*N*S), 400 µM dNTPs (equal mixture of each of dATP, dCTP, dGTP, dTTP), and 0.3 µM phi29 DNA polymerase (200 ng per 10 µL reaction). The amplification reaction was performed in 50 mM HEPES buffer (pH=8.0) containing 15 mM KCl, 20 mM MgCl2, 0.01% (v/v) Tween-20, 1 mM TCEP, and 1:10,000 (v/v) SYBR Green I, by incubating the reaction mixture at about 30° C. Real-time data was collected in Tecan fluorescent plate reader by monitoring the SYBR Green fluorescence using an excitation wavelength of 485 nm and an emission wavelength of 535 nm.

Following the amplification, the amplification products were restriction digested using EcoR1. Briefly, 2 µL of amplified product was mixed with 1 µL of EcoR1 (10 Units/µL), 1 µL 10× NE buffer, and 6 µL distilled water (total volume of 10 µL). The mixture was incubated at 37° C. for 1 h. The digested products in each tube was mixed with 3 µL of loading dye (2 µL 6× loading buffer+1 µL 1:200 Pico Green) and loaded in 0.8% agarose gel. 1 Kb Plus DNA Ladder was used in the marker lane (9 µL TE buffer, 2 µL 6× loading buffer, 1 µL 1:200 Pico Green and 1 µL of 1 Kb Plus DNA Ladder (1 µg/µL) were mixed together and loaded 10 µL on the gel).

Figure 9:
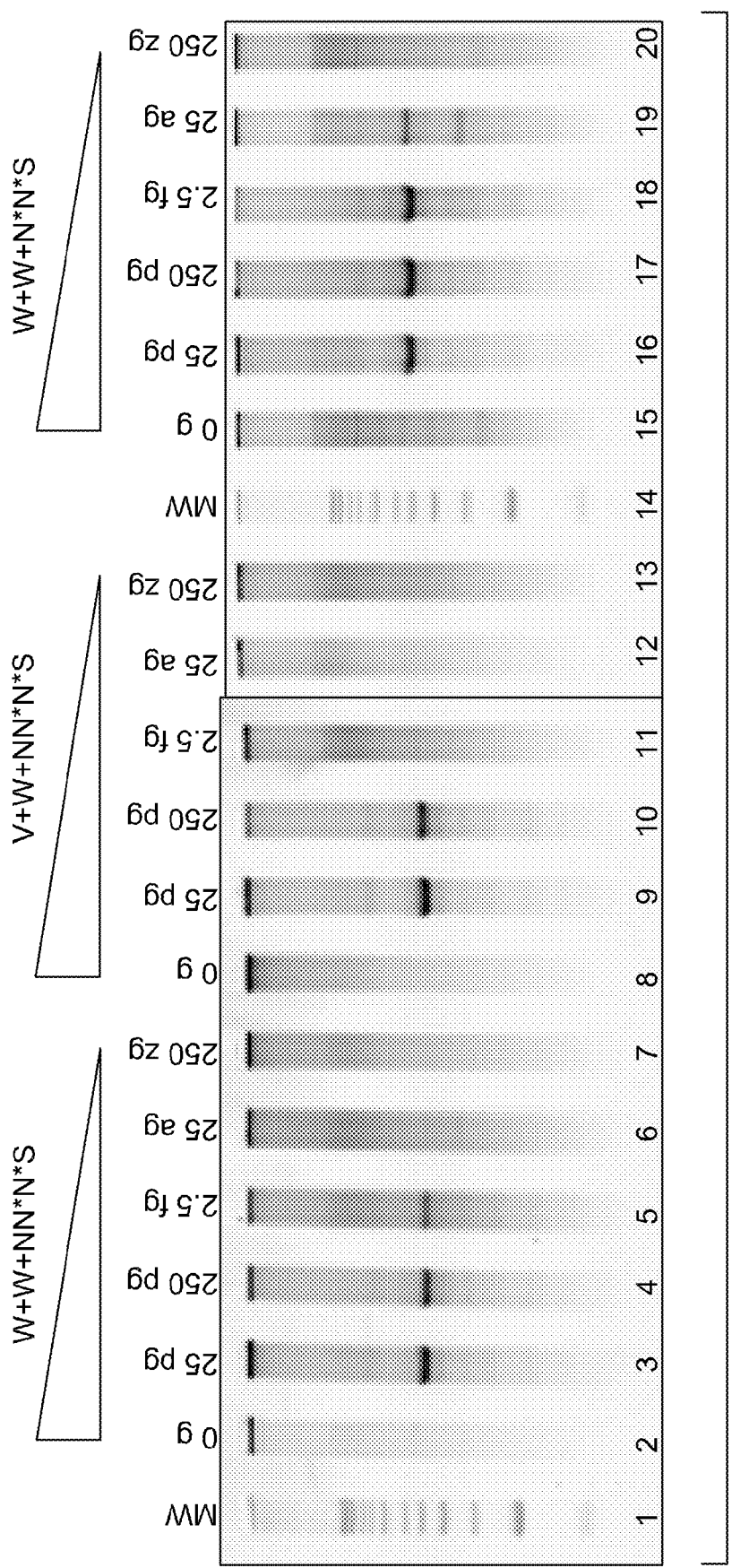
FIG. 9 shows DNA amplification efficiencies of a partially constrained pentamer primer or partially constrained hexamer primers with respect to varying target DNA template concentration according to some embodiments of the invention.

FIG. 9 shows the agarose gel of the EcoR1 restriction digest of amplification products using various primer compositions. The pentamer primer W+W+N*N*S was found to be marginally better than that of the hexamer primer W+W+ NN*N*S.

The precise use, choice of reagents, choice of variables such as concentration, volume, incubation time, incubation temperature, and the like may depend in large part on the particular application for which it is intended. While only certain features of the invention have been illustrated and described herein, it is to be understood that one skilled in the art, given the benefit of this disclosure, will be able to identify, select, optimize or modify suitable conditions for using the methods in accordance with the principles of the present invention, suitable for these and other types of applications.

The foregoing examples and embodiments are illustrative of some features of the invention rather than limiting on the invention described herein. They are selected embodiments or examples from a manifold of all possible embodiments or examples. The invention may be embodied in other specific forms without departing from the spirit or essential characteristics thereof. It is, therefore, to be understood that the appended claims are intended to cover all modifications and changes that fall within the true spirit of the present invention.

What is claimed is:

1. A method for nucleic acid amplification, comprising:
   providing a nucleic acid template;
   contacting the nucleic acid template with a primer solution, wherein the primer solution consists essentially of a partially constrained primer mixture comprising a terminal mismatch primer-dimer structure; and
   amplifying the nucleic acid template,
   wherein extension of the terminal mismatch primer-dimer structure during the step of amplifying the nucleic acid template is inhibited.

2. The method of claim 1, wherein the amplification step is performed, at least in part, under isothermal conditions.

3. The method of claim 1, wherein the partially constrained primer is a hexamer primer, a pentamer primer, a tetramer primer, or a combination thereof.

4. The method of claim 1, wherein the partially constrained primer is a pentamer primer, the nucleotide sequence of which consists of WWNNS.

5. The method of claim 1, wherein the partially constrained primer is a hexamer primer, the nucleotide sequence of which consists of WWNNNS.

6. The method of claim 1, wherein the partially constrained primer comprises a nucleotide analogue.

7. The method of claim 6, wherein the nucleotide analogue is a LNA nucleotide.

8. The method of claim 1, further comprising adding a nucleic acid polymerase and deoxyribonucleoside triphosphates before the amplification step.

9. The method of claim 8, wherein the nucleic acid polymerase comprises a strand displacing nucleic acid polymerase.

10. The method of claim 8, wherein the nucleic acid polymerase comprises a Phi29 DNA polymerase.

11. The method of claim 1, wherein the nucleic acid amplification comprises a rolling circle amplification, or a multiple displacement amplification.

12. A method for isothermal nucleic acid amplification, comprising:
    providing a nucleic acid template;
    contacting the nucleic acid template with a primer solution, wherein the primer solution consists essentially of a partially constrained primer mixture, and wherein the partially constrained primer mixture comprises a nucleotide analogue; and
    amplifying the nucleic acid template under isothermal conditions.

13. The method of claim 12, wherein the isothermal nucleic acid amplification comprises a rolling circle amplification, or a multiple displacement amplification.

14. The method of claim 12, wherein the nucleic acid template is a circular DNA template or a linear DNA template.

15. The method of claim 12, wherein the partially constrained primer has a terminal mismatch primer-dimer structure.

16. The method of claim 12, wherein the partially constrained primer comprises a 3' terminal nucleotide and a 5' terminal nucleotide, which are non-complementary to each other.

17. The method of claim 16, wherein the 3' terminal nucleotide of the partially constrained primer is further non-complementary to a nucleotide adjacent to the 5' terminal nucleotide.

18. The method of claim 12, wherein the partially constrained primer consists of a nucleotide sequence $(W)_x(N)_y(S)_z$, wherein x, y and z are integer values independent of each other, and wherein value of x is 2 or 3, value of y is 2, 3 or 4, and value of z is 1 or 2.

19. The method of claim 12, wherein the nucleotide analogue is an LNA nucleotide.

20. The method of claim 19, wherein the partially constrained primer is a pentamer primer, the nucleotide sequence of which consists of +W+WNNS, or W+W+NNS.

21. The method of claim 19, wherein the partially constrained primer is a hexamer primer, the nucleotide sequence of which consists of +W+WNNNS, or W+W+NNNS.

22. The method of claim 12, wherein the partially constrained primer comprises a phosphorothioate linkage between a 3' terminal nucleotide and a nucleotide that is adjacent to the 3' terminal nucleotide.

23. The method of claim 22, wherein the partially constrained primer is a pentamer primer, the nucleotide sequence of which consists of W+W+NN*S, or +W+WNN*S.

24. The method of claim 22, wherein the partially constrained primer is a hexamer primer, the nucleotide sequence of which consists of W+W+NNN*S, +W+WNNN*S.

25. The method of claim 22, wherein the partially constrained primer is a pentamer primer, the nucleotide sequence of which consists of W+W+N*N*S, or +W+WN*N*S.

26. The method of claim 22, wherein the partially constrained primer is a hexamer primer, the nucleotide sequence of which consists of W+W+NN*N*S, or +W+WNN*N*S.

27. A method for nucleic acid amplification, comprising:
    providing a nucleic acid template;
    contacting the nucleic acid template with a primer solution, wherein the primer solution consists essentially of a nuclease-resistant, partially constrained primer mixture to form a nucleic acid template-primer complex, wherein the nuclease-resistant, partially constrained primer mixture comprises a modified nucleotide, and wherein the nuclease-resistant, partially constrained primer mixture comprises a terminal mismatch primer-dimer structure;
    contacting the nucleic acid template-primer complex with a Phi29 polymerase and deoxyribonucleoside triphosphates; and
    amplifying the nucleic acid template,
    wherein extension of the terminal mismatch primer-dimer structure during the step of amplifying the nucleic acid template is inhibited.

28. The method of claim 27, wherein the nucleic acid template is amplified by rolling circle amplification, or by multiple displacement amplification.

* * * * *